(12) United States Patent
Doerr et al.

(10) Patent No.: US 11,684,787 B2
(45) Date of Patent: Jun. 27, 2023

(54) IMPLANTABLE SYSTEM FOR THE DIAGNOSTIC AND/OR THERAPEUTIC TREATMENT OF A HUMAN PATIENT OR AN ANIMAL PATIENT

(71) Applicant: BIOTRONIK SE & CO. KG, Berlin (DE)

(72) Inventors: Thomas Doerr, Berlin (DE); Sergey Ershov, Berlin (DE); Torsten Radtke, Berlin (DE); Martin Roemer, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 50 days.

(21) Appl. No.: 16/835,619

(22) Filed: Mar. 31, 2020

(65) Prior Publication Data
US 2020/0330779 A1 Oct. 22, 2020

(30) Foreign Application Priority Data
Apr. 18, 2019 (DE) .............................. 102019110283

(51) Int. Cl.
*A61N 1/37* (2006.01)
*A61N 1/372* (2006.01)
(Continued)

(52) U.S. Cl.
CPC ........... *A61N 1/37282* (2013.01); *A61N 1/08* (2013.01); *A61N 1/3621* (2013.01);
(Continued)

(58) Field of Classification Search
CPC .... A61N 1/362; A61N 1/3621; A61N 1/3622; A61N 1/3624; A61N 1/368; A61N 1/37264
See application file for complete search history.

(56) References Cited

U.S. PATENT DOCUMENTS 5,653,735 A 8/1997 Chen et al.
6,068,651 A 5/2000 Branded
(Continued)

FOREIGN PATENT DOCUMENTS

DE 69633211 T2 8/2005

*Primary Examiner* — Allen Porter
(74) *Attorney, Agent, or Firm* — Laurence A. Greenberg; Werner H. Stemer; Ralph E. Locher

(57) ABSTRACT

An implantable system for the diagnostic and/or therapeutic treatment of a human or animal patient contains a processor, a memory, a treatment unit and a remote data transmission unit. The system is characterized in that the memory includes a computer-readable program which prompts the processor to carry out the following steps when the program is being executed on the processor: a) ascertaining whether a treatment functionality of the treatment unit could jeopardize a patient in whom the system was implanted if a diagnostic and/or therapeutic treatment of the patient corresponding to the treatment functionality were to be carried out; b) deactivating the treatment functionality when a potential risk for the patient was ascertained; c) receiving reactivation data by way of the remote data transmission unit; and d) reactivating the deactivated treatment functionality based on the received reactivation data.

11 Claims, 9 Drawing Sheets

(51) Int. Cl.
  *A61N 1/39* (2006.01)
  *G16H 20/00* (2018.01)
  *A61N 1/08* (2006.01)
  *A61N 1/36* (2006.01)
  *A61N 1/362* (2006.01)
(52) U.S. Cl.
  CPC ..... *A61N 1/36128* (2013.01); *A61N 1/39622* (2017.08); *G16H 20/00* (2018.01)

(56) References Cited

U.S. PATENT DOCUMENTS

| | | | |
|---|---|---|---|
| 6,195,584 B1 | 2/2001 | Hill et al. | |
| 6,876,880 B2 | 4/2005 | Hess et al. | |
| 7,107,098 B2 | 9/2006 | Sharma et al. | |
| 7,167,755 B2 | 1/2007 | Seeberger et al. | |
| 7,280,869 B2 | 10/2007 | Warman et al. | |
| 7,769,453 B2 | 8/2010 | Doerr et al. | |
| 2003/0097154 A1* | 5/2003 | Henry | A61N 1/3622 607/5 |
| 2003/0120317 A1 | 6/2003 | Hess et al. | |
| 2004/0167579 A1 | 8/2004 | Sharma et al. | |
| 2006/0074463 A1 | 4/2006 | Seeberger et al. | |
| 2007/0250131 A1 | 10/2007 | Doerr et al. | |
| 2012/0109237 A1* | 5/2012 | Xiao | A61N 1/3622 607/5 |
| 2013/0261473 A1* | 10/2013 | Xi | A61B 5/0215 600/486 |
| 2013/0345536 A1 | 12/2013 | Doerr | |
| 2016/0030743 A1* | 2/2016 | Kaiser | A61N 1/36514 607/14 |
| 2016/0228701 A1* | 8/2016 | Huelskamp | A61N 1/3622 |
| 2017/0312514 A1* | 11/2017 | Hareland | A61N 1/37252 |

* cited by examiner

IMPLANTABLE SYSTEM FOR THE DIAGNOSTIC AND/OR THERAPEUTIC TREATMENT OF A HUMAN PATIENT OR AN ANIMAL PATIENT

CROSS-REFERENCE TO RELATED APPLICATION

This application claims the priority, under 35 U.S.C. § 119, of German patent application DE 10 2019 110 283, filed Apr. 18, 2019; the prior application is herewith incorporated by reference in its entirety.

BACKGROUND OF THE INVENTION

Field of the Invention

The present invention relates to an implantable system for the diagnostic and/or therapeutic treatment of a human patient or an animal patient according to the preamble of the independent implantable system claim, to a treatment system comprising such an implantable system according to the preamble of the independent treatment system claim, to a method for controlling the operation of such an implantable system according to the preamble of the independent method claim, and to a computer program product according to the preamble of the independent computer program product claim.

Implantable systems for treating, and in particular for stimulating, a human heart or an animal heart, such as cardiac pacemakers, have been known for quite some time. These can carry out a variety of functions. It is known, among other things, to use such cardiac pacemakers for treating atrial arrhythmia. Different stimulation programs may be carried out by a corresponding cardiac pacemaker in the process so as to return the treated heart to a normal state.

However, it is frequently difficult to predict which type of treatment is useful for adequately and effectively treating arrhythmia, and in particular atrial tachycardia.

U.S. Pat. No. 6,876,880 B2, for example, describes the option of different atrial pacing therapies being applied consecutively. The US patent furthermore describes that the success of the treatment is dependent on the condition of the heart. As a result, the US patent furthermore opens up the option of repeating atrial pacing therapies that were previously unsuccessful once a predetermined period of time has passed or the condition of the heart has changed otherwise. In this way, an improved treatment of atrial arrhythmia is to be achieved. However, this procedure yields only moderate success since ultimately this requires a spontaneous change in the condition of the heart or the passing of a sufficiently long period of time.

U.S. Pat. No. 7,107,098 B2 describes a method and a device for generating and selecting therapies, or hierarchies of therapies, suitable for treating atrial or ventricular tachycardia. It is provided to store an effectiveness of a therapy achieved in the past, and to then assign a higher hierarchy to this therapy.

U.S. Pat. No. 7,280,869 B2 describes a method for determining whether a tachyarrhythmia episode has been terminated. A heart beat pattern is used for this determination, which represents a sequence of atrial and ventricular depolarizations.

Moreover, implants having therapeutic and diagnostic functions are already known from the prior art, in which these functions are automatically deactivated when a potential risk for the patient by these functions is identified. So as to reactivate these functions, it has been necessary until now for the patient to see a physician, who then reactivates the previously deactivated function(s) during what is known as an in-office follow-up.

This procedure, however, is very complex and requires patients—in addition to visits to general practitioners—to see physicians specialized in implants having therapeutic and diagnostic functions. It would be desirable to be able to reduce the number of required visits so as to ensure greater patient comfort and relief for heavily frequented doctor's offices.

SUMMARY OF THE INVENTION

It is the object of the present invention to provide an implant having a diagnostic and/or therapeutic function which enables greater patient comfort and reduces the follow-up complexity in doctor's offices, while meeting the safety standards known from the prior art for avoiding a risk for the patient.

This object is achieved by an implantable system for the diagnostic and/or therapeutic treatment of a human patient or an animal patient having the features of the independent implantable system claim. Such a system comprises a processor, a memory unit, a treatment unit, and a remote data transmission unit. The treatment unit is used to carry out a diagnostic and/or therapeutic treatment of the patient in whom the system was implanted. By way of the remote data transmission unit, data can be transmitted to a receiver located remotely in relation of the implantable system via remote data transmission networks, which are known per se, such as WLAN or mobile radio communication, and in particular wirelessly.

According to the invention, it is provided that the memory unit comprises a computer-readable program, which prompts the processor to carry out the steps described hereafter when the program is being executed on the processor.

Initially, it is ascertained whether a treatment functionality of the treatment unit could jeopardize a patient in whom the system was implanted if a diagnostic and/or therapeutic treatment of the patient which corresponds to the treatment functionality were to be carried out by way of the treatment unit. It is thus ascertained in advance whether such a patient risk could exist with a planned (but not yet administered) treatment.

When such a possible patient risk was ascertained, the corresponding treatment functionality is deactivated. The treatment unit typically includes a plurality of different treatment functionalities. Typically, each of these treatment functionalities can be deactivated independently of other treatment functionalities. It is also possible to jointly deactivate certain treatment functionalities that form a group.

As a result of the deactivation, a therapeutic or diagnostic treatment of the patient defined by the treatment functionality can no longer be carried out by the treatment unit. This is not possible again until the treatment functionality was reactivated. As was already mentioned at the outset, the approaches known from the prior art require a patient to see a specialist to have the treatment functionality reactivated.

According to the presently claimed invention, however, a step of receiving reactivation data now takes place by way of the remote data transmission unit. It is thus possible by way of the presently claimed invention to send reactivation data to the implantable system via the remote data transmission unit.

The deactivated treatment functionality is then reactivated based on the received reactivation data. If different treatment functionalities were previously deactivated, the reactivation data can include information as to which of the deactivated treatment functionalities are to be reactivated. It is also possible to always reactivate all previously deactivated treatment functionalities by way of the received reactivation data.

As a result of a reactivation of the treatment functionality, a diagnostic and/or therapeutic treatment corresponding to the treatment functionality can subsequently be carried out again.

It is provided that the reactivation data can only be transmitted to the implantable system by trained medical staff, in particular physicians, specialized in such implantable systems. It is then possible to ensure that the treatment functionality is only reactivated if a risk for the patient is no longer presumed to exist. At the same time, however, it is not necessary for the patient to see the corresponding physician or trained medical staff. This avoids needless travel for the patient, and saves the physician from having unnecessary patient visits.

In one variant, the program prompts the processor to send status data by way of the remote data transmission unit. This status data indicates whether a particular treatment functionality of the treatment unit is activated or deactivated. This status data can then be received by a remotely situated computer (for example, at a physician specializing in implants). The physician or another user of the remotely situated computer is then able to identify which treatment functionalities of the implantable system were deactivated, so as to decide whether a reactivation of these treatment functionalities is in the interest of the patient. The status data—as well as the reactivation data in this or in other exemplary embodiments—can be transmitted in encrypted form. The sufficiently known, conventional encryption mechanisms are suitable for this purpose.

In one variant, it is possible to permit individual treatment functionalities to be reactivated, while disallowing a reactivation of other treatment functionalities. For this purpose, one or more treatment functionalities can be assigned to a first group, and one or more other treatment functionalities can be assigned to a second group. The two groups can subsequently be treated differently with respect to the reactivation. Specifically, the program prompts the processor in this variant to permit a reactivation of one or more treatment functionalities assigned to the first group, based on the received reactivation data. At the same time, the program prompts the processor to disallow a reactivation of individual or multiple treatment functionalities assigned to the second group. Providing different groups thus enhances the patient's safety since certain treatment functionalities that pose a particularly high risk for the patient can thus be precluded in a targeted manner from being reactivated by way of remote data transmission. So as to reactivate such functions, it is still necessary to see a physician specialized in implantable systems, who is then able to carry out a corresponding reactivation after having examined the patient.

So as to assign individual or multiple treatment functionalities to the first group or to the second group, the processor uses assignment data in one variant. This assignment data can be stored in the memory unit of the implantable system or be transmitted to the system by other means. Such assignment data makes it possible to flexibly assign treatment functionalities to the first group or to the second group. For example, such assignment data can provide that a particular treatment functionality is to be assigned to the first group at a first point in time. At a later point in time, such assignment data can prompt an assignment of the same treatment functionality to the second group. The assignment data can, for example, take a state of health of the patient into consideration which affords or necessitates a facilitated or more difficult reactivation of particular treatment functionalities.

In one variant, assignment data is precluded from being transmitted to the implantable system by way of the remote data transmission device.

In one variant, the system comprises a near field telemetry unit. In this variant, the program prompts the processor to receive assignment data by way of the near field telemetry unit. In this way, it is possible to clear certain treatment functionalities for reactivation, or to exclude these from reactivation, and more particularly, for example, when the patient is visiting a physician not specialized in implants, such as his or her primary care physician. The primary care physician is then not able to directly initiate a reactivation of individual previously deactivated treatment functionalities. However, it is possible for the primary care physician to clear certain treatment functionalities by way of the near field telemetry unit. Subsequently, reactivation data can then be transmitted by a specialist to the implantable system and received by the same by way of the remote data transmission unit. In this way, access to the implantable system would be subject to dual control. On the one hand, certain treatment functionalities have to be cleared for reactivation by way of the near field telemetry unit. On the other hand, a physician specialized in implants or accordingly trained medical staff additionally has to send reactivation data to the implantable system. Such a multi-stage safety procedure makes it possible to significantly reduce a risk due to unauthorized access to the implantable system. Nonetheless, the patient has to see only one physician, who moreover does not need to be a specialist for implants.

The assignment data transmitted to the implantable system by way of the near field telemetry unit or by other means can, for example, allow a temporary assignment of certain treatment functionalities to the first group of treatment functionalities. It may then be possible, for example, to permit a reactivation of the previously deactivated treatment functionality within a time window having a duration of, for example, 1 minute to 10 hours, in particular 5 minutes to 5 hours, in particular 10 minutes to 2 hours, in particular 20 minutes to 1.5 hours, and in particular 30 minutes to 1 hour. Subsequently, the corresponding treatment functionality is automatically assigned to the second group. A reactivation of the treatment functionality is then no longer possible. If no reactivation has taken place within the time window, initially new assignment data has to be transmitted to the implantable system so as to reopen the fundamental option of reactivating the deactivated treatment functionality.

In one variant, the implantable system is a system for treating, and in particular for stimulating, a human hear or an animal heart. For example, the system can be a cardiac pacemaker, which has different functionalities. The system can, for example, be an implantable system for stimulating a human heart or an animal heart, which is provided and configured to apply atrial antitachycardia pacing. However, arbitrary other functionalities are also conceivable.

In one variant, the system can also be a medical product, which is used for entirely different diagnostic and/or therapeutic applications within a patient. Examples include implantable defibrillators, neurostimulators, implantable medical pumps and ventricular assist devices.

In one variant, the treatment unit includes at least one treatment functionality, which is selected from the group consisting of ventricular pacing, ventricular conditioning stimulation, atrial pacing, atrial antitachycardia pacing and defibrillation. Ventricular pacing may, for example, be right ventricular overdrive pacing, left ventricular overdrive pacing, or biventricular overdrive pacing. Biventricular overdrive pacing can be carried out, for example, with a VV delay deviating from a regular stimulation. Specific adaptations of the ventricular conditioning stimulation to previously detected atrial tachycardia, as they are described elsewhere in the present application, are likewise conceivable.

One aspect of the present invention relates to a treatment system comprising an implantable system for the diagnostic and/or therapeutic treatment of a human patient or an animal patient according to the above descriptions, and a remote access unit disposed remotely therefrom. As described, the implantable system comprises a first processor, a first memory unit, a treatment unit, and a first remote data transmission unit. The remote access unit comprises a second processor, a second memory unit, and a second remote data transmission unit. The remote access unit can be a conventional computer. The first memory unit includes a first computer-readable program, which prompts the first processor to carry out the steps described hereafter when the program is being executed on the first processor.

Initially, it is ascertained whether a treatment functionality of the treatment unit could jeopardize a patient in whom the system was implanted if a diagnostic and/or therapeutic treatment of the patient which is specified by the treatment functionality were to be carried out.

When such a potential patient risk was ascertained, the treatment functionality is deactivated. The treatment defined by the treatment functionality can then no longer be carried out.

If thereafter reactivation data is received by way of the first remote data transmission unit, the deactivated treatment functionality may subsequently be reactivated, taking the received reactivation data into consideration.

The second memory unit includes a second computer-readable program, which prompts the second processor to carry out the steps described hereafter when the program is being executed on the processor.

Reactivation data is generated in response to an input or a program request. This reactivation data is then transmitted by way of the second remote data transmission unit. The steps of generating the reactivation data and of transmitting the reactivation data are typically carried out prior to the step of receiving the reactivation data by way of the first remote data transmission unit. It is possible in the process and contemplated that the reactivation data has already been generated and is only transmitted by way of the second remote data transmission unit when a reactivation of a particular treatment functionality becomes necessary, so that the data can be received by way of the first data transmission unit.

An input that prompts the generation of reactivation data can, for example, be a user input on the remote access unit. For example, after having been informed that a particular implantable system has deactivated a treatment functionality, which is now to be reactivated, a physician is able to prompt a generation of reactivation data by an input on a user interface. For this purpose, the physician can previously obtain assurance, by telephone or other means, that a reactivation of the treatment functionality no longer poses a risk for the patient, for example because the condition of the patient has since changed.

In one variant, the second program prompts the second processor to receive status data of the implantable system prior to the generation of the reactivation data by way of the second remote data transmission unit. This status data indicates whether a particular treatment functionality of the treatment unit is activated or deactivated. The reason is that reactivation data with respect to a treatment functionality only has to be transmitted when this treatment functionality has in fact been deactivated. The status data can also indicate whether or not a remote reactivation of the respective treatment functionality is permissible.

For example, it is possible that a physician tasked with the reactivation of a treatment functionality first checks the status of the corresponding implantable system. This can take place based on such status data, which is transmitted from the first remote data transmission unit to the second remote data transmission unit. When the physician then recognizes that a particular treatment functionality was deactivated, but he or she also has information that a risk to the patient no longer exists as a result of a change in the patient's condition that has since taken place, the physician is able to generate the required reactivation data in the remote access unit. Such a change in the patient's condition may have occurred, for example, as a result of a treatment with pharmaceuticals.

In one variant, it is provided that the fundamental option of reactivating a treatment functionality cannot be altered remotely. When a treatment functionality is thus labeled to the effect that it is not reactivatable remotely, it is not possible for a physician to implement a change to this labeling by way of remote access to the effect that a reactivation by way of remote access is made possible after all. Rather, in one variant, an interaction with the implantable system in much greater proximity, for example through direct access or access by way of a near field telemetry unit, is required for this purpose. In this way, unauthorized access to the implantable system and the activity status of the individual treatment functionalities is made significantly more difficult.

One aspect of the present invention relates to a method for controlling the operation of an implantable system for the diagnostic and/or therapeutic treatment of a human patient or an animal patient according to the above descriptions. This method comprises the steps described hereafter.

Initially, it is ascertained whether a treatment functionality of a treatment unit of the system could jeopardize a patient in whom the system was implanted if a diagnostic and/or therapeutic treatment of the patient defined by the treatment functionality were to be carried out.

When such a possible patient risk is identified, the treatment functionality is deactivated.

Only after reactivation data has been received by way of a remote data transmission unit can the deactivated treatment functionality be reactivated, based on the received reactivation data. If, in contrast, such reactivation data is not received, the treatment functionality remains in the deactivated state thereof.

One aspect of the present invention relates to a computer program product including computer-readable code, which prompts a processor to carry out the steps described hereafter when the code is being executed on the processor.

Initially, it is ascertained whether a treatment functionality of a treatment unit of an implanted system for the diagnostic and/or therapeutic treatment of a human patient or an animal patient could jeopardize a patient in whom the system was implanted if a diagnostic and/or therapeutic treatment of the patient defined by the treatment functionality were to be carried out.

When such a potential patient risk was ascertained, the treatment functionality is deactivated.

A reactivation of the treatment functionality is only possible when reactivation data is available. This reactivation data is received by way of a remote data transmission unit. After having been received, the reactivation data can be used to reactivate the previously deactivated treatment functionality. If no reactivation data is received, the treatment functionality remains in the deactivated state thereof.

One aspect of the present invention relates to a method for treating a human patient or an animal patient in need of such treatment. This treatment is carried out by way of an implantable system for the diagnostic and/or therapeutic treatment. The system comprises a processor, a memory unit, a treatment unit, and a remote data transmission unit. The method comprises the steps described in greater detail hereafter.

Initially, it is ascertained whether a treatment functionality of the treatment unit could jeopardize a patient in whom the system was implanted if a diagnostic and/or therapeutic treatment of the patient defined by the treatment functionality were to be carried out.

When such a potential patient risk was ascertained, the treatment functionality is deactivated. It remains in the deactivated state thereof until it is reactivated based on reactivation data.

Such reactivation data can be received by way of the remote data transmission unit. After the reactivation data has been received, it is possible to reactivate the previously deactivated treatment functionality.

Thereafter, a diagnostic and/or therapeutic treatment of the patient defined by the treatment functionality can be carried out.

One aspect of the present invention relates to an implantable system for stimulating a human heart or an animal heart, having the features described hereafter. Such a system is intended, in particular, for the permanent implantation in a human patient or an animal patient. When the system is to be implanted in an animal patient, the patient is preferably a mammal, for example a mammal selected from the group consisting of rodents, horses, dogs and cats.

The system comprises a processor, a memory unit, an atrial stimulation unit, a ventricular stimulation unit, and a first detection unit. The first detection unit is used to detect atrial tachycardia, that is, the atrium of the heart beating at an abnormally increased rate.

According to the invention, the system is characterized in that the memory unit includes a computer-readable program, which prompts the processor to carry out the steps described hereafter when the program is being executed on the processor.

First, it is detected by way of the first detection unit whether atrial tachycardia to be treated is present in a human heart or an animal heart of the patient in whom the implantable system was implanted. This type of tachycardia, which can also be referred to as tachycardia requiring treatment, is characterized in that the atrial rhythm exceeds a critical rate and/or the resulting ventricular rhythm exceeds or drops below a critical rate and/or the atrial rhythm is classified as unstable and/or the beats of the resulting ventricular rhythm exhibit appreciable fluctuations.

In addition to non-pathological atrial tachycardia, the term 'atrial tachycardia requiring treatment' also encompasses pathological atrial tachycardia, which is also known under the designation 'atrial fibrillation.' In one variant, the method carried out by the processor refers only to non-pathological atrial tachycardia or only to pathological atrial tachycardia.

When atrial tachycardia to be treated is present, a ventricular conditioning stimulation is carried out by way of the ventricular stimulation unit. This ventricular conditioning stimulation brings the heart into a state in which it is more receptive to subsequent atrial stimulation. The heart is thus brought very deliberately into a state in which it exhibits increased susceptibility toward subsequent treatments. As a consequence, the system claimed according to the invention does not wait for the heart to assume a different state by itself or by prior atrial treatments. Rather, an active change in the cardiac state is brought about by way of a ventricular conditioning stimulation. A multitude of conditioning stimulations that are known per se are possible to achieve such a change in the cardiac state.

As the ventricular conditioning stimulation is being carried out and/or thereafter, atrial antitachycardia pacing is applied. The atrial stimulation unit is used for this purpose. Such atrial antitachycardia pacing is also known by the technical term 'atrial ATP' (the abbreviation ATP denoting antitachycardia pacing). ATP is also at times referred to as antitachycardia pacemaker therapy.

Since the heart, as a result of the concurrent or prior ventricular conditioning stimulation, is considerably more susceptible to the applied atrial ATP than without ventricular conditioning stimulation, the success of the atrial ATP therapy can be enhanced. This makes it possible for the heart of the treated patient to beat more quickly again at a normal beat, and for pathological consequences of the atrial tachycardia, such as declines in performance, dizziness and thrombus formation, to occur far less frequently.

In one variant, the atrial antitachycardia pacing is only applied while the ventricular conditioning stimulation is being carried out. In another variant, atrial antitachycardia pacing is only applied after the ventricular conditioning stimulation has been carried out. In another variant, the atrial antitachycardia pacing is applied both as the ventricular conditioning stimulation is being carried out and thereafter.

In one variant, the atrial stimulation unit is designed to apply the atrial antitachycardia pacing in the form of electrical stimulation or in the form of optical stimulation. As a result, this offers different options for treating the detected atrial tachycardia. Different treatment variants may be selected, in particular taking into account the severity of the detected atrial tachycardia.

In one variant, the program prompts the processor to carry out the ventricular conditioning stimulation in the form of right ventricular overdrive pacing. During overdrive pacing, the corresponding ventricle is stimulated using a rate higher than the customary (intrinsic) ventricle rate. In this way, an increase in the rate of the ventricular rhythm can be achieved.

In another variant, the program prompts the processor to carry out the ventricular conditioning stimulation in the form of left ventricular overdrive pacing. The ventricular conditioning stimulation can thus deliberately influence, and in particular increase, only the rate of the ventricular rhythm of a single ventricle.

In another variant, it is provided that the program prompts the processor to stimulate both ventricles equally. In this case, the ventricular conditioning stimulation is carried out in the form of biventricular overdrive pacing. In this way, it is possible to achieve a simultaneous increase in the rate of the intrinsic ventricular rhythm of both ventricles.

In one variant, the program prompts the processor to carry out the ventricular conditioning stimulation in the form of biventricular overdrive pacing, and to specify a VV time deviating from a regular stimulation. The VV time (also referred to as VV delay) indicates the time that passes between the stimulation of the right and the left ventricle. It is also referred to as intraventricular delay. When both ventricles are stimulated at the same time, the VV delay is zero. Typically, however, it is greater than zero so as to achieve that the left ventricle is stimulated later than the right ventricle. Selecting a VV delay deviating from a regular stimulation results in a change in the cardiac state, whereby the heart is more susceptible toward concurrently or subsequently applied atrial antitachycardia pacing.

In one variant, the program prompts the processor to carry out the ventricular conditioning stimulation so that ventricular pauses are compensated for. This can be achieved, for example, by an intensity of the ventricular conditioning stimulation and/or by setting the VV delay and/or by delivering additional ventricular stimuli and/or by setting alternative ventricular stimulation vectors (such as between the right and left ventricular electrodes).

In one variant, the program prompts the processor to couple the ventricular conditioning stimulation with a short AV delay to the detected atrial tachycardia. A ratio of n:1 is specified in the process. Specifically, the program prompts the processor to couple the ventricular conditioning stimulation with an AV delay of 10 to 110 ms to detected actions of the atrial tachycardia at a ratio of n:1, wherein n corresponds to the number of detected actions of the atrial tachycardia, and n is 2 to 6. The AV time (also referred to as AV delay) indicates the time that passes between a stimulation of the right atrium and the right ventricle. It is also referred to as atrioventricular delay. When this AV delay is minimized, and moreover the ventricular conditioning stimulation is adapted to the detected atrial tachycardia, a particularly advantageous reaction of the heart thus treated to the ventricular conditioning stimulation is to be expected, so that concurrent or subsequent atrial antitachycardia pacing can be applied particularly effectively.

In one variant, the program prompts the processor to carry out the ventricular conditioning stimulation in a manner so as to achieve a particular physiological objective. For example, the conditioning stimulation can be carried out in such a way that the pressure in the left and/or right atria is lowered at least briefly. As an alternative or in addition, the conditioning stimulation can be carried out in such a way that the risk of mitral valve regurgitation is reduced at least briefly or entirely avoided. As an alternative or in addition, the conditioning stimulation can be carried out in such a way that the preload of the heart is reduced at least briefly. As an alternative or in addition, the conditioning stimulation can be carried out in such a way that the blood pressure of a patient whose heart is being stimulated by the implantable system is lowered at least briefly. As an alternative or in addition, the conditioning stimulation can finally be carried out in such a way that a myocardial oxygen balance is improved at least briefly. All of these effects—either individually or in any arbitrary combination—achieve a change in the cardiac state, which enhances a susceptibility of the heart to concurrently or subsequently applied atrial antitachycardia pacing.

In one variant, the implantable system comprises a second detection unit, which is used to detect an effect of the ventricular conditioning stimulation on the atrial antitachycardia pacing. As a result of this second detection unit, which can also comprise parts of the first detection unit, it is thus possible to directly or indirectly detect the cardiac effect achieved by the ventricular conditioning stimulation. In this way, the overall effectiveness of the stimulation carried out by the implantable system can be improved. The reason is that it is possible, in this way, to obtain positive feedback about the achieved effect with respect to the cardiac state. The second detection unit can, for example, use the same electrode that is also used by the first detection unit. It is thus conceivable, in principle, for the second detection unit to detect the effect of the ventricular conditioning stimulation in the atrium of the treated heart.

In one variant, the program prompts the processor to store a success of the atrial antitachycardia pacing therapy and the ventricular conditioning stimulation carried out in connection with this pacing therapy. It is thus possible to create value pairs, which each encompass the success of the atrial antitachycardia pacing therapy and the ventricular conditioning stimulation carried out at the same time or beforehand. It is then possible to select at least one value pair from the stored value pairs for a subsequent treatment of the heart. For example, the value pair for which the best outcome of the atrial antitachycardia pacing therapy was achieved can be selected. Similarly, for example, a value pair for which the desired success of the atrial antitachycardia pacing therapy could not be achieved, despite ventricular conditioning stimulation, can be excluded. Storing can take place in the memory unit of the implantable system. As an alternative, another memory unit can be provided in the implantable system, which is used to store the value pairs.

One aspect of the invention relates to a method for controlling the operation of the implantable system for stimulating a human heart or an animal heart. This method comprises the steps described hereafter.

First, it is detected by way of a first detection unit whether atrial tachycardia to be treated (requiring treatment) is present in a human heart or an animal heart.

If this is the case, at least one impulse is generated for a ventricular conditioning stimulation in a ventricular stimulation unit. Instead of a single pulse, it is also possible to select a pulse sequence including pulses having the same amplitude or different amplitudes and a constant, increasing or decreasing rate.

Simultaneously with and/or after the generation of the at least one pulse in the ventricular stimulation unit, at least one pulse for atrial antitachycardia pacing is generated in an atrial stimulation unit. This at least one pulse can, for example, likewise be a pulse sequence including different pulses having the same amplitude or amplitudes of different magnitudes, wherein the rate between the individual pulses can be designed to be constant, increasing or decreasing. This method thus relates to the generation of at least one ventricular conditioning stimulation pulse and at least one atrial stimulation pulse within the implantable system.

One aspect of the present invention relates to a non-volatile computer program product including computer-readable code, which prompts a processor to carry out the steps described hereafter when the code is being executed on the processor.

First, it is detected by way of a first detection unit whether atrial tachycardia to be treated is present in a human heart or an animal heart.

When atrial tachycardia to be treated is present, a ventricular conditioning stimulation is carried out by way of a ventricular stimulation unit.

As the ventricular conditioning stimulation is being carried out and/or thereafter, atrial antitachycardia pacing is applied by way of an atrial stimulation unit.

One aspect of the present invention relates to a method for treating a human patient or an animal patient in need of such treatment. This treatment is carried out by way of an implantable system for stimulating the heart of the patient. The system comprises a processor, a memory unit, an atrial stimulation unit, a ventricular stimulation unit, and a first detection unit for detecting atrial tachycardia. The method comprises the steps described hereafter.

First, it is detected by way of the first detection device whether atrial tachycardia to be treated is present in the heart.

When such atrial tachycardia requiring treatment was detected, a ventricular conditioning stimulation is carried out by way of the ventricular stimulation unit.

During or after the ventricular conditioning stimulation, atrial antitachycardia pacing is applied by way of the atrial stimulation unit. This method thus has a direct therapeutic effect on the treated human or animal heart so as to treat detected atrial tachycardia, and to return the treated heart, and in particular the atrium of the treated heart, to a customary rhythm.

One aspect of the present invention relates to an implantable system for treating a human heart or an animal heart, having the features described hereafter. Such a system comprises a processor, a memory unit, a treatment unit comprising a treatment electrode, and a detection unit for detecting cardiac events requiring treatment. According to the invention, the system is characterized in that the memory unit includes a computer-readable program, which prompts the processor to carry out the steps described hereafter when the program is being executed on the processor.

First, it is detected by way of the detection device whether a cardiac event to be treated has occurred in the human or animal heart. This cardiac event can, for example, be a cardiac rhythm disturbance, such as atrial or ventricular tachycardia, or cardiac arrest.

When a cardiac event to be treated was detected, initially no treatment of this cardiac event is carried out yet. Rather, a position of the treatment electrode is first determined. Instead of a position of the treatment electrode, it is also possible to determine a variable correlating with this position. A position of a treatment electrode shall be understood to mean the position of a conducting section of the treatment electrode. Such a conducting section is also referred to as an electrode pole.

Thereafter, the position of the treatment electrode or the variable correlating with the position is compared to a reference variable. A cardiac treatment by way of the treatment unit and the treatment electrode is carried out when the position of the treatment electrode, or when the variable correlating with the position, agrees with the reference variable within a predefinable tolerance.

If the ascertained position of the treatment electrode or the variable correlating with the position does not agree with the reference variable within a predefinable tolerance, the position of the treatment electrode is inadequate. In this case, (initially) no cardiac treatment is carried out. The reason is that the damage from such a cardiac treatment could be greater than the benefit. When, for example, two electrodes are located too close together, or one electrode is no longer disposed in the atrium, but in the ventricle of a heart, carrying out a cardiac treatment could result in undesirable side effects, some of which are serious, which are to be avoided.

The reference variable, including the tolerance thereof, is determined so that a position of the treatment electrode is considered to be inadequate when treatment success is unlikely due to such a position, applying the treatment could result in side effects with (potentially not foreseeable) consequences, or when delivering the treatment could have damaging consequences for the treated heart.

In any case, the actually required cardiac treatment is refrained from being carried out until a decision has been made as to whether a treatment should nonetheless be carried out, despite the position of the treatment electrode having been established to be inadequate. The reason is that, even when a position of the treatment electrode was ascertained to be inadequate, at times the benefit of a cardiac treatment that is nonetheless carried out could be greater than any anticipated damage. In one variant, the option of a manual or automated intervention in the program executed by the processor is thus provided so as to still enable cardiac treatment, even when the established position of the treatment electrode initially does not support such a treatment. When considering a severity of the detected cardiac event to be treated, and the deviation of the position of the treatment electrode from the reference variable, however, it may be useful or necessary for saving the life of a patient to carry out a treatment even if success of the therapy is questionable or if (serious) side effects are feared.

The system is suitable for temporary or permanent implantation, wherein, in particular, a permanent implantation of the system in a human patient or an animal patient is intended. When the system is to be implanted in an animal patient, the patient is, in particular, a mammal, for example a mammal selected from the group consisting of rodents, horses, dogs and cats.

The treatment unit and the treatment electrode, which can also be referred to as the therapy unit and the therapy electrode, can be a unit and an electrode suitable for any type of treatment of a human heart or an animal heart. For example, the treatment electrode can be a stimulation electrode used to stimulate human or animal heart tissue. The treatment electrode can also be a defibrillation electrode. The exact configuration of the treatment electrode is not of particular significance for the presently claimed invention.

In one variant, the implantable system comprises more than one treatment unit and more than one treatment electrode. In particular, it is provided that one treatment electrode is provided for each cardiac region to be treated. Multiple treatment electrodes can be connected to a single treatment unit. Typically, however, exactly one treatment unit is assigned to each treatment electrode.

In an alternative embodiment, the implantable system comprises more than one detection unit. Again, one detection unit can be provided for each cardiac region to be treated. The different cardiac regions to be treated can be, for example, the left atrium, the left ventricle, the right atrium or the right ventricle of a human heart or an animal heart.

In one variant, the position of the treatment electrode to be determined is a relative position of the treatment electrode with respect to a reference point of the system. This reference point can be another treatment electrode of the system, for example. The reference point can also be a reference electrode of the system. For example, a portion of the housing of the implantable system can be configured in the form of a reference electrode.

In one variant, the relative position of the treatment electrode or the variable correlating with this relative position is determined by determining a distance between the treatment electrode and the reference point. This distance is then compared to a reference distance, which serves as a reference variable. Such a distance determination makes it possible to ascertain whether a relative displacement of the considered electrodes has taken place. It is possible to determine a single distance between the treatment electrode and the reference point, or two or more distances between different treatment electrodes and/or between one or more treatment electrodes and a reference electrode. It is possible to apply differing weightings to the individual distances when calculating a variable correlating with the distance. In this way, it is possible to assign a higher weighting to a relative change in position of an electrode in the case of which a change in position can have particularly serious consequences for a successful treatment, than to a relative change in position of an electrode in the case of which a change in position can have a less serious effect on a successful treatment.

In principle, different options exist for ascertaining the absolute or relative position of the treatment electrode. In one variant, the program prompts the processor to determine the relative position of the treatment electrode by measuring an electrical current and/or by measuring a voltage between the treatment electrode and the reference point. When, for example, the distance between different treatment electrodes or between a treatment electrode and a reference electrode is to be determined, a voltage is applied between these electrodes. One of the electrodes serves as a current sink in the process. Respective electrode pairs are then selected from two of the considered n electrodes, and the voltage present between these electrodes is determined. When the implantable system comprises a total of n electrodes (treatment electrodes and reference electrodes), this results in $$\frac{n!}{(n-2)!\,2!} = \binom{n}{2}$$

electrode combinations that can be used for a corresponding voltage determination. For example, if there are n=4 electrodes, $$\binom{4}{2} = \frac{4*3*2*1}{2*1*2*1} = 6$$

combinations result for a selection of two electrodes.

It is provided in one embodiment of the invention to apply voltages between at least two to no more than n−1 electrode poles. Thereafter, the voltage between electrode poles is measured, of which at least one pole is not involved in the generation of the voltage.

Furthermore, according to another embodiment of the invention, an electrical current is feed between at least two to no more than n−1 electrode poles. At least one electrode pole serves as a current sink in the process. Thereafter, the voltage or the current between at least two of the n electrode poles is measured.

According to a preferred exemplary embodiment of the invention, the electrical current and/or the voltage are delivered by way of at least one treatment electrode and measured by way of at least one treatment electrode and/or reference electrode. The measurement is carried out immediately after the delivery of the electrical current and/or the voltage, so that an effect generated by the fed current/the applied voltage can be measured directly. The effect can be a physiological effect generated by the current/the voltage.

In one variant, the reference point or the reference electrode is situated in the area of the thorax of the patient. As was already described, a portion of the housing of the implantable system can serve as the reference electrode. The distance between the electrodes situated in the heart and the reference electrode is then comparatively large.

In one variant, the voltage applied to the electrodes has a frequency in a range of 0 to 1 MHz, in particular 0.1 to 0.9 MHz, in particular 0.2 to 0.8 MHz, in particular 0.3 to 0.7 MHz, in particular 0.4 to 0.6 MHz, and in particular 0.5 to 1 MHz.

In one variant, the voltage applied to the electrodes is a pulsed voltage having a pulse duration in a range of 10 µs to 100 ms, in particular 100 µs to 10 ms, in particular 500 µs to 5 ms, in particular 750 µs to 2.5 ms, in particular 900 µs to 2 ms, and in particular 1 ms to 1.5 ms.

In one variant, the intervals between the individual pulses can cover a very wide range, in terms of time. For example, it is possible to consecutively emit a plurality of pulses in very short succession for determining the position of the treatment electrode, so as to then have a longer pause until the next position determination. In one variant, the times that pass between individual pulses can thus be 10 µs to 2 years, in particular 50 µs to 1.9 years, in particular 100 µs to 1.8 years, in particular 1 ms to 1.7 years, in particular 500 ms to 1.6 years, in particular 1 second to 1.5 years, in particular 10 seconds to 1.4 years, in particular 1 minute to 1.3 years, in particular 10 minutes to 1.2 years, in particular 1 hour to 1 year, in particular 1 day to 0.5 years, in particular 1 week to 0.25 years, and in particular 2 weeks to 1 month. It is also conceivable that the pulse spacing during individual measurements is in an interval made up of the shorter time periods (for example 10 µs to 1 second) and the spacing between pulses of different measurements is in an interval made up of the longer segments (for example 1 minute to 2 years). Of course, all of the intervals explicitly mentioned above or the intervals to be formed otherwise of the upper and lower values delimiting these intervals can be used for the duration of the pulse spacing.

In one embodiment, a measurement comprises a plurality of individual measuring pulses, which are emitted in the form of so-called bursts.

In one variant, at least one measurement is carried out per year, so as to enable continuous position monitoring of the treatment electrode.

In one variant, the measurement of the voltage applied to the electrodes or of the currents introduced into the electrodes is carried out in the form of an impedance measurement. For example, 2-pole, 3-pole and/or 4-pole impedance measuring methods can be employed for this purpose.

In one variant, the current fed into the electrodes or the voltage applied to the electrodes can be measured directly by way of the electric fields generated in the body of the patient. In an alternative embodiment, moreover an indirect measurement is also contemplated. The reason is that the applied voltage or the fed current causes excitation of a cardiac region in which one of the electrodes involved in the measurement is positioned, which subsequently spreads to another cardiac region. This results in a physiological delay of the excitation propagation. Based on the pattern of the excitation propagation and/or the physiological delay of the excitation propagation, it is possible to determine the effect of the fed current or of the applied voltage.

The current or the voltage generates electric fields that cause a particular effect in the body. This effect and/or the effect determined indirectly via the delayed physiological effect of the current or the voltage represents a characteristic parameter for the position of the treatment electrode, and in particular for the distance between the treatment electrode and a reference point, such as a reference electrode. This parameter is a variable correlating with the position within the meaning of the present invention.

In an alternative embodiment, it is also contemplated to measure both an immediate (direct) effect of the fed current or of the applied voltage and a delayed physiological effect of the current or the voltage and to use this for determining the position of the treatment electrode.

In an alternative, the processor is prompted by the program to assess the detected delayed physiological effect. In particular, it is provided to carry out a plausibility check so as to check whether the reason for the detected physiological delay is the assumed position of the treatment electrode. Limiting values can be predefined for this plausibility check, which has to be adhered to within a likewise predefinable tolerance range. If an excessively large delayed physiological effect or an excessively small delayed physiological effect is detected, this plausibility check may cause the obtained result not to be considered to be outside the range to be adhered to from the outset. Rather, this may be an indication that the measurement is faulty and has to be repeated. In contrast, there are many reasons that support the assumption that the measured position of the treatment electrode corresponds to the actual position thereof, in particular when only minor deviations from the presumed position are established during the plausibility check. It is then possible to ascertain in a subsequent step whether this position in fact agrees with the reference variable for this position within the predefinable tolerance.

Whenever a predefinable value is described or explained within the scope of the present application, this value can be fixedly predefined or freely programmable, for example. In such a case, it is also possible for a corresponding value to be selected from a plurality of exemplary values. These exemplary values can be predefined in ranges meaningful for the particular application and, for example, can be made available for selection in what experience has shown to be realistic intervals.

In one variant, it is ascertained based on a direct effect of the electric fields generated in the body whether a permitted minimum distance between two electrodes is adhered to or not met. For example, it is possible to check that a measurement signal ascertained as a result of an applied voltage or a fed current does not exceed a threshold value serving as the reference variable. If the threshold value is not exceeded, the minimum distance is adhered to.

In one variant, the sensitivity of the ascertainment of a distance between two electrodes can be increased by combining different measurement methods with one another. For example, when the ascertainment of the immediate effect of the applied voltage or of the fed current has already yielded the result that a drop below the minimum distance did not occur, it can additionally be checked that the physiologically delayed effect achieved by the applied voltage or the fed current does not drop below a predefinable delay period. If a drop below the defined delay period does not occur, two confirmations obtained by different measurement methods exist that a drop below the minimum distance between the electrodes did not occur.

In one variant, it is provided that the position of the treatment electrode is an absolute position of the treatment electrode within a human heart or an animal heart when the system is implanted in a human or an animal. This means that the position, in this case, is determined independently of other components of the then implanted system. The expression "absolute position" denotes the arrangement of the treatment electrode in the heart or in a particular cardiac region.

So as to make such an absolute position determination of the treatment electrode possible, the treatment electrode comprises an acceleration sensor in one variant. Such an acceleration sensor, which can be configured, for example, as a linear acceleration sensor or a rotation rate sensor or gyroscope, can be used to track a movement of the treatment electrode within the heart.

In one variant, it is provided for this purpose that the program prompts the processor to create an acceleration profile of the treatment electrode by way of acceleration data collected by the acceleration sensor. Moreover, the processor is prompted to correlate this acceleration profile with the cardiac rhythm of the human or animal heart in which the corresponding treatment electrode is situated. In this way, it is possible to ascertain whether the treatment electrode is tracking the movements of the cardiac region in which the treatment electrode is situated or presumed. If the acceleration profile of a ventricular treatment electrode is synchronous with the ventricular cardiac rhythm of the corresponding ventricle, the treatment electrode is still situated in the ventricle in which it was originally disposed. If, in contrast, a correlation of the acceleration profile of the treatment electrode and the cardiac rhythm of a particular cardiac region shows that the treatment electrode is tracking the movements of a cardiac region in which it is not supposed to be situated (for example, an atrial treatment electrode tracks a ventricular cardiac rhythm), this demonstrates that the treatment electrode is no longer situated in the cardiac region in which it was originally disposed. This means that a dislocation of the treatment electrode has taken place, which regularly precludes this treatment electrode from being activated for carrying out a cardiac therapy. The reason is that the expected therapy success would then not materialize. Rather, (serious) side effects of a corresponding cardiac treatment would have to be expected. A relocation of the treatment electrode would have to be carried out first here, so that the desired treatment success can in fact be achieved.

In one variant, data is also collected by sensors that are situated outside the human or animal heart and that are not influenced by the movements of the heart, during the determination of the absolute position of the treatment electrode. By including such supplemental sensor data, it is possible to reduce, or even eliminate, artefacts that may occur elsewhere. This increases the accuracy of the determination of the absolute position of the treatment electrode.

In one variant, the system comprises a patient state sensor. Such a patient state sensor is used to determine a body position or an activity state of a patient in whom the system was implanted. Such a patient state sensor may be a position sensor, for example, which can be used to ascertain whether the patient is in an upright position or a horizontal position. For example, a sensor that can be used to monitor the heart rate of the patient is a patient state sensor suitable for determining the activity state of the patient. The heart rate is typically monitored directly by one or more electrodes of the system for treating the heart, so that the sensors already present in the system can assume the function of the patient state sensor, which is why a separate patient state sensor is not necessarily required in such a case. Detecting the body position or the activity state of the patient makes it possible to collect additional data, which increases the reliability of the remaining measurement data since it can provide an explanation for potentially abnormal measurement data.

In one variant, the program prompts the processor to store a progression of the position of the treatment electrode over time. In this way, it is possible to establish a trend of the position of the treatment electrode. For example, an onsetting dislocation of the treatment electrode can thus be identified at an early stage, when a change in the position of the treatment electrode that, per se, is still within the predefined tolerance range is found, and, at the same time, it is evident that this change in position is taking place in exactly one direction (for example, an increasing distance or a decreasing distance). Such an analysis of the progression of the position of the treatment electrode can also be used to ascertain the positional stability of the treatment electrode. In this way, for example, an imminent loose connection of the treatment electrode can be identified at an early stage.

In one variant, the program prompts the processor to store only those values of the position of the treatment electrode which were collected when the patient was in a defined body position and/or in a defined activity state. The data collected by the optionally provided patient state sensor is preferably used for this purpose. By limiting the values of the position of the treatment electrode to be stored, an overall more reliable trend of a change in the position of the treatment electrode can be ascertained. The reason is that overall improved comparability of the stored values is achieved when the measurements that were obtained for assessing the position of the treatment electrode are only stored when they relate to a comparable body position of the patient or a comparable activity state of the patient. It is then possible to provide more precise information as to the positional stability of the treatment electrode. In this way, artefacts are minimized or eliminated.

In one variant, the program prompts the processor to carry out a position determination of the treatment electrode even when no cardiac treatment of the corresponding human or animal heart is to be carried out. In this way, it is possible to collect measurement data independently of a cardiac treatment, which provides insights into the position of the treatment electrode. When such data is collected at regular or irregular intervals, information as to the positional stability of the treatment electrode can be provided. An (onsetting) dislocation of the treatment electrode can thus be identified at an early stage, which may then possibly be corrected even before the need to carry out a cardiac treatment.

In one variant, the program prompts the processor to carry out a cardiac treatment after a presettable time has elapsed or in response to a signal if a cardiac event to be treated was established beforehand. This cardiac treatment takes place in such a case by way of the treatment unit and the treatment electrode, regardless of the previously ascertained position of the treatment electrode. This means that this safety step makes a cardiac treatment possible even if an inadequate position of the treatment electrode was ascertained. The reason is that, at times, the established deviation of the position of the treatment electrode from the expected position is comparatively small, while the cardiac event to be treated is comparatively serious. Taking the patient's interest into consideration, it may be more advantageous on an overall basis to carry out a cardiac treatment, and accept side effects, than to suppress such a cardiac treatment.

An external input signal generated by a physician can, for example, be a signal that prompts the processor to carry out a cardiac treatment, regardless of the ascertained position of the treatment electrode. As a result, a physician—taking the patient's interest and the medical risk of a cardiac treatment into consideration—has the option to carry out a cardiac treatment, despite a seemingly or effectively dislocated treatment electrode.

In one variant, the system comprises at least one device for emitting and/or receiving acoustic waves. This device is used to determine the position of the treatment electrode. The acoustic waves can be ultrasonic waves, for example. An emitter for acoustic waves can be disposed on the treatment electrode, for example. A receiver for the acoustic waves emitted by the emitter can be disposed on the reference point. By way of signal attenuation, taking place after the acoustic waves have been emitted, and/or a phase shift compared to the fed acoustic signal, it is then possible to obtain additional information about the distance between the treatment electrode and the reference point. The delay that results from the acoustic signal propagation in the heart or in the body of the patient is orders of magnitude shorter than a physiological delay of the excitation propagation caused by the introduction of a current pulse into the heart. By a combined evaluation of the immediate effect of a fed current or an applied voltage by way of the electric fields generated thereby in the heart and/or the delayed physiological excitation as a result of the applied voltage or the fed current and/or the emitted and received acoustic signals, it is thus possible to work in up to three different levels of time, which allows a very precise position determination of the treatment electrode.

It is also possible to dispose the emitter of the acoustic waves or acoustic signals on the reference point, instead of on the electrode, and to dispose the receiver on the electrode. At the same time, it is possible to use a transceiver for acoustic signals instead of a receiver that is separate from the emitter. It is also possible to provide the emitter, the receiver or the transceiver on a different component of the implantable system, instead of on the electrode. In such a case, it is useful to provide a reflective element on the electrode, which reflects the acoustic signals directed at the electrode. In such a case, it is possible to collect relevant data for the determination of the distance between the electrode and the emitter, the receiver or the transceiver from the progression of the acoustic signals toward the electrode and/or away from the electrode.

In one variant, the system comprises at least one device for emitting and/or receiving electromagnetic waves. This embodiment of the device is used to determine the position of the treatment electrode distance measurement using electromagnetic waves. The electromagnetic waves can have a frequency in the range of 1 MHz to 1 GHz, in particular of 10 MHz to 900 GHz, in particular of 100 MHz to 800 GHz, in particular of 500 MHz to 700 GHz, in particular of 1 GHz to 600 GHz, in particular of 10 GHz to 500 GHz, in particular of 100 GHz to 400 GHz, and in particular of 200 GHz to 300 GHz. The electromagnetic waves are galvanically fed into the tissue.

In one variant, the electromagnetic waves are fed into the cardiac tissue in the frequency range of 300 MHz to the infrared range, that is, 300 GHz. Thereafter, it is possible to ascertain a distance between the treatment electrode and the reference point based on a transmission measurement of the electromagnetic waves. According to an exemplary embodiment of the present invention, it is possible to use electromagnetic waves in the visible frequency range instead of acoustic waves. Suitable frequency ranges are between 400 THz and 800 THz, in particular between 500 THz and 700 THz, and in particular between 550 THz and 650 THz. Emitters and receivers or transceivers can also be used in the case of electromagnetic waves. It is possible, but not mandatory, to arrange an emitter, a receiver or a transceiver on the electrode. It is likewise possible to use reflective elements, which reflect the electromagnetic waves, but this is only useful for certain frequency ranges. The reason is that, in particular, light in the visible range penetrates only short distances in the human tissue, so that the luminous intensity may potentially already be too low once a reflective element is reached. Lower-frequency electromagnetic waves, however, have a larger range in human tissue, so that reflections are possible here. Instead of simple transmission measurements, combined reflection and transmission measurements are also possible.

In one variant, the cardiac event to be detected which is to be treated by way of the implantable system is atrial tachycardia. In such a case, the cardiac treatment is atrial antitachycardia pacing. The treatment electrode may also be referred to as a stimulation electrode in this case.

One aspect of the present invention relates to a method for controlling the operation of an implantable system for treating a human heart or an animal heart, and in particular to an implantable system according to the above description. This method comprises the steps described hereafter.

First, it is detected by way of a detection unit whether a cardiac event to be treated has occurred in a human heart or an animal heart.

If a cardiac event to be treated has occurred, a position of a treatment electrode is determined. As an alternative or in addition, a variable correlating with this position of the treatment electrode can be determined.

Subsequently, the position of the treatment electrode or the variable correlating with the position is compared to a reference variable.

When the position of the treatment electrode or the variable correlating with the position agrees with the reference variable within a predefinable tolerance, an impulse for a cardiac treatment is generated in a treatment unit of the system. This impulse can then be forwarded via a treatment electrode.

If, in contrast, the position of the treatment electrode or the variable of the treatment electrode correlating with the position does not agree with the reference variable within a predefinable tolerance, no impulse for a subsequent cardiac treatment is generated in the treatment unit.

One aspect of the present invention relates to a non-volatile computer program product including computer-readable code, which prompts a processor to carry out the steps described hereafter when the code is being executed on the processor.

First, it is detected by way of a detection device whether a cardiac event to be treated has occurred in the human or animal heart.

When a cardiac event to be treated was detected, initially no treatment of this cardiac event is carried out yet. Rather, a position of a treatment electrode is first determined. Instead of a position of the treatment electrode, it is also possible to determine a variable correlating with this position.

Thereafter, the position of the treatment electrode or the variable correlating with the position is compared to a reference variable. A cardiac treatment by way of the treatment unit to which the treatment electrode is assigned is carried out when the position of the treatment electrode, or when the variable correlating with the position, agrees with the reference variable within a predefinable tolerance.

If the ascertained position of the treatment electrode or the variable correlating with the position does not agree with the reference variable within a predefinable tolerance, the position of the treatment electrode is inadequate. In this case, (initially) no cardiac treatment is carried out. The reason is that the damage from such a cardiac treatment could be greater than the benefit.

A further aspect of the present invention relates to a method for treating a human patient or an animal patient requiring such treatment, by way of an implantable system for treating a human heart or an animal heart, wherein the system comprises a processor, a memory unit, a treatment unit comprising a treatment electrode, and a detection unit for detecting a cardiac event requiring treatment. The method comprises the steps described hereafter.

First, it is detected by way of the detection unit whether a cardiac event to be treated has occurred in the heart of the patient.

If a cardiac event to be treated has occurred, a position of the treatment electrode or a variable correlating with this position is determined.

The position of the treatment electrode or the variable correlating with the position is then compared to a reference variable.

When the position of the treatment electrode or the variable correlating with the position agrees with the reference variable within a predefinable tolerance, a cardiac treatment is carried out by way of the treatment unit and the treatment electrode.

In contrast, when the position of the treatment electrode or the variable correlating with the position does not agree with the reference variable within a predefinable tolerance, initially no cardiac treatment is carried out by way of the treatment unit and the treatment electrode.

One aspect of the present invention relates to an implantable system for stimulating a human heart or an animal heart, having the features described hereafter. Such a system is intended, in particular, for the permanent implantation in a human patient or an animal patient. When the system is to be implanted in an animal patient, the patient is preferably a mammal, for example a mammal selected from the group consisting of rodents, horses, dogs and cats.

The system comprises a processor, a memory unit, an atrial stimulation unit, and a detection unit for detecting atrial tachycardia.

According to the invention, it is provided that the memory unit comprises a computer-readable program, which prompts the processor to carry out the steps described hereafter when the program is being executed on the processor.

First, it is detected by way of the detection unit whether atrial tachycardia to be treated is present in a human heart or an animal heart.

When such atrial tachycardia to be treated was detected, atrial antitachycardia pacing is applied by way of the atrial stimulation unit.

After the atrial antitachycardia pacing has been applied, an atrial post-treatment stimulation is carried out. In particular, the atrial stimulation unit is likewise used for this purpose. The post-treatment stimulation causes a change in the cardiac state, whereby the long-term therapy success rate of the atrial overstimulation, which was carried out within the scope of the atrial antitachycardia pacing, is increased. As a result of the atrial post-treatment, overall a sustained effect of the atrial antitachycardia pacing therapy is achieved. The reason is that the treated heart, as a result of the atrial post-treatment, has a lesser tendency toward returning into a state of atrial tachycardia.

In one variant, the program prompts the processor, after the atrial antitachycardia pacing has been applied, to initially check by way of the detection unit whether the atrial tachycardia was terminated by the conducted stimulation. Thus, a termination detection of the atrial tachycardia is carried out. Only when the termination of the atrial tachycardia was positively ascertained is the atrial post-treatment stimulation carried out. In this way, it is achieved that the atrial post-treatment stimulation is carried out at a point in time at which the treated heart no longer requires atrial antitachycardia pacing for terminating the previously detected atrial tachycardia.

In one variant, the program prompts the processor to carry out the atrial post-treatment stimulation as atrial overstimulation. This atrial overstimulation is delimited with respect to the atrial antitachycardia overstimulation by being designed to be longer than atrial antitachycardia overstimulation, that is, in the range of minutes up to days. According to one embodiment, the atrial post-treatment is configured to be within a range of up to 7 days, 6 days, 5 days, 4 days, 3 days, 2 days or 1 day. According to further embodiments, the atrial post-treatment is configured to be within a range of up to 120 minutes, 60 minutes, 30 minutes, 20 minutes, 10 minutes, 5 minutes, 4 minutes, 3 minutes, 2 minutes, 1 minute or 0.5 minute. Moreover, the atrial post-treatment stimulation according to the invention differs from the known antitachycardia overstimulation by only being invoked when no tachycardiac intrinsic (heart's own) atrial activity is present, that is, for example, when the atrial intrinsic heart rhythm is less than 100 bpm. According to a particularly advantageous embodiment of the invention, the atrial post-treatment stimulation is delivered using a stimulation rate of less than or equal to 200 bpm, 180 bpm, 150 bpm, 140 bpm, 130 bpm, 120 bpm, 110 bpm, or 100 bpm. By comparison, stimulation rates of 375 bpm are used for the known antitachycardia overstimulation, or rates of up to 3000 bpm (50 Hz) in the case of high-frequency bursts.

In one variant, the atrial post-treatment stimulation is carried out in the form of right atrial overdrive pacing. During such overdrive pacing, the corresponding atrium is stimulated using a rate higher than the customary (intrinsic) non-tachycardiac atrial rate. However, the stimulation rate for overdrive pacing is less than for atrial antitachycardia pacing (for example, less than or equal to 130 bpm).

In another variant, the program prompts the processor to carry out the atrial post-treatment stimulation in the form of left atrial overdrive pacing. The atrial post-treatment stimulation can thus deliberately influence the rate of the atrial rhythm of a single atrium, and in particular delay the return from a tachycardia state into a normal state.

In another variant, it is provided that the atrial post-treatment stimulation is designed as biatrial overdrive pacing. In such a case, the program prompts the processor to increase the atrial rate of the rhythm of both atria.

Such an overdrive post-treatment of one or both atria brings the heart more slowly back into the normal state after atrial antitachycardia pacing than if no post-treatment stimulation were carried out. As a result, a gentle transition between atrial antitachycardia pacing and the normal heart rhythm is achieved, which results in a mild treatment of the heart and ensures a more sustained effect of the atrial antitachycardia pacing therapy.

In one variant, the program prompts the processor to carry out the atrial post-treatment stimulation during a first duration. This first duration is specifiable in the process. It is thus a defined time period in a range of 1 minute to 7 days.

In one variant, the atrial post-treatment stimulation is not carried out for a (fixed) time period, but uses the heart rhythm of the treated patient for reference. In this variant, the program thus prompts the processor to carry out the atrial post-treatment stimulation during a defined number of cardiac cycles. In this variant, it is possible to address the different heart rhythms of the individual patients even more specifically, which can further enhance the lasting success of the post-treatment stimulation.

In one variant, the program prompts the processor to carry out the atrial post-treatment stimulation in a manner that achieves a particular physiological objective. For example, the post-treatment stimulation can be carried out in such a way that the pressure in the left and/or right atrium is lowered at least briefly. As an alternative or in addition, the post-treatment stimulation can be carried out in such a way that the risk of mitral valve regurgitation is reduced at least briefly or entirely avoided. As an alternative or in addition, the post-treatment stimulation can be carried out in such a way that the preload of the heart is reduced at least briefly. As an alternative or in addition, the post-treatment stimulation can be carried out in such a way that the blood pressure of a patient whose heart is being stimulated by the implantable system is lowered at least briefly. As an alternative or in addition, the post-treatment stimulation can finally be carried out in such a way that a myocardial oxygen balance is improved at least briefly. All of these effects—either individually or in any arbitrary combination—achieve a change in the cardiac state, which increases the lasting effect of the previously applied atrial antitachycardia pacing, and thereby improves the success of the atrial antitachycardia pacing therapy.

In one variant, the atrial stimulation unit is designed to apply the atrial antitachycardia pacing and/or the atrial post-treatment stimulation in the form of electrical stimulation or in the form of optical stimulation. In this way, it is possible to apply not only the atrial antitachycardia pacing therapy, but also the atrial post-treatment stimulation, by employing different physical mechanisms of action. The different available treatment variants can, in particular, be selected by taking the severity of the detected atrial tachycardia, and the resultant post-treatment stimulation that is useful to carry out, into consideration.

One aspect of the present invention relates to a method for controlling the operation of an implantable system for stimulating a human heart or an animal heart. This method is suitable, in particular, for controlling the operation of an implantable system according to the above descriptions. This control method comprises the steps described hereafter.

First, it is detected by way of a detection device whether atrial tachycardia to be treated is present in a human heart or an animal heart.

When such atrial tachycardia to be treated was detected, at least one impulse for atrial antitachycardia pacing is generated in an atrial stimulation unit.

After the impulse for the atrial antitachycardia pacing therapy has been generated, at least one impulse for an atrial post-treatment stimulation is generated in the atrial stimulation unit. Previously, it can be checked whether atrial tachycardia to be treated is still present in the human or animal heart. The generation of the at least one impulse for the atrial post-treatment stimulation can be made dependent on whether a termination of previously detected atrial tachycardia requiring treatment was ascertained. An appropriate detector signal can serve as an input variable for the control method for this purpose.

One aspect of the present invention relates to a computer program product including computer-readable code, which prompts a processor to carry out the steps described hereafter when the code is being executed on the processor.

First, it is detected by way of a detection device whether atrial tachycardia to be treated is present in a human heart or an animal heart.

When such atrial tachycardia to be treated was detected, atrial antitachycardia pacing is carried out by way of an atrial stimulation unit.

After the atrial antitachycardia pacing has been applied, in particular likewise by way of the atrial stimulation unit, an atrial post-treatment stimulation is carried out.

One aspect of the present invention relates to a method for treating a human patient or an animal patient in need of such treatment. An implantable system for stimulating the heart of the patient is used in the process. This system comprises a processor, a memory unit, an atrial stimulation unit, and a detection unit for detecting atrial tachycardia. The treatment method comprises the steps described hereafter.

First, it is checked by way of the detection unit whether atrial tachycardia to be treated is present in the heart of the patient.

When such atrial tachycardia was detected, atrial antitachycardia pacing is applied by way of the atrial stimulation unit.

After the atrial antitachycardia pacing has been applied, an atrial post-treatment stimulation is carried out. This atrial post-treatment stimulation brings the heart of the patient more slowly into a normal state having a common heart rhythm than if the atrial antitachycardia pacing therapy were ended abruptly. As a result of this gentler transition to a common heart rhythm, a sustained and longer lasting effect of the applied atrial antitachycardia pacing therapy is achieved.

One aspect of the present invention relates to an implantable system for stimulating a human heart or an animal heart, having the features described hereafter. Such a system is intended, in particular, for the permanent implantation in a human patient or an animal patient.

Such an implantable system comprises a processor, a memory unit, a stimulation unit, and a first detection unit for detecting a cardiac rhythm disturbance of a heart region.

According to the invention, it is provided that the memory unit comprises a computer-readable program, which prompts the processor to carry out the steps described hereafter when the program is being executed on the processor.

First, it is detected by way of the first detection unit whether a cardiac rhythm disturbance is present in a cardiac region of a heart of a human patient or an animal patient. A presence of a cardiac rhythm disturbance within the meaning of the present invention is to be presumed if the onset or the presence of a cardiac rhythm disturbance can be detected.

If such a cardiac rhythm disturbance was identified, a suitable stimulation strategy is selected based on a selection criterion. The selection criterion includes a measurement variable or a variable calculated from the measurement variable. The measurement variable is selected from the group consisting of a physiological measurement variable of the patient, a pathophysiological measurement variable of the patient, and a non-physiological measurement variable indicating a state of the patient. In particular, the group available for selection is composed of the above-described measurement variables or a subset thereof. The selection criterion can comprise more than one of these measurement variables, which can also be arithmetically related to one another. A different weighting of individual or all measurement variables is possible.

According to one embodiment, the condition of the heart is detected prior to the aATP delivery. The condition can be mapped using different parameters, which are described within the scope of the invention. A suitable point in time for delivery of the aATP therapy, having a high likelihood of success of the therapy, can be ascertained based on at least one of these parameters.

Afterwards, the cardiac region in which the cardiac rhythm disturbance was detected is stimulated using the selected stimulation strategy. The stimulation unit is used for this purpose. The stimulation unit can be an atrial stimulation unit or a ventricular stimulation unit. It is possible to stimulate one atrium or both atria and/or one ventricle or both ventricles using the stimulation unit. The stimulation of the cardiac region or of the cardiac regions is carried out with the objective of terminating the detected cardiac rhythm disturbance. For example, the cardiac rhythm disturbance can be atrial tachycardia/tachyarrhythmia (AT) or atrial fibrillation (AFib). As a result of the selected stimulation strategy, ideally a stimulation is carried out which results in a termination of the detected cardiac rhythm disturbance, such as the detected AT/AFib, within a short time period, using the least amount of energy possible, and the termination success of which is long-lasting, that is, a long duration passes until AT/AFib occurs again.

Thereafter, a success and/or an efficiency of the conducted stimulation are detected. This can take place by way of the first detection unit and/or a further detection unit of the system.

The detected success and/or the detected efficiency are now compared to a predefinable success and/or efficiency criterion. In this way, it is possible to determine whether a desired success or a desired efficiency was able to be achieved. A success of a stimulation is, for example, that a normal heart rhythm is restored. Indicators for the efficiency of a conducted stimulation are, for example, the time required for restoring a normal heart rhythm, the energy required to do so, or also the time that passes between the first AT/AFib termination and the renewed occurrence of AT/AFib. If this time increases for successive AT/AFib, this speaks in favor of the effectiveness of the stimulation according to the invention.

If the predefinable success and/or efficiency criterion was achieved, no adaptation of the stimulation strategy is required. Rather, the selected stimulation strategy is then already sufficiently successful or sufficiently efficient for the treated cardiac rhythm disturbance. If, in contrast, the predefinable success and/or efficiency criterion was not achieved, the stimulation strategy is optimized, so that better success and/or greater efficiency can be achieved during a subsequent stimulation using an optimized stimulation strategy. The optimization of the stimulation strategy includes a change in the stimulation strategy with respect to at least one parameter. This parameter is selected from the group consisting of a form of the treatment, a number of the treatments, a combination of different treatments, a frequency of the treatments, and a point in time of the treatment. In particular, the group is composed of the above-described parameters or a subset thereof.

The expression "form of the treatment" shall, in particular, be understood to mean a design and/or a pattern of electrical pulses that are delivered within the scope of a stimulation by the stimulation unit.

The point in time of the treatment can be selected in such a way, for example, that particularly good success or a particularly high efficiency of the stimulation is to be expected. The reason is that a stimulation which is delivered during a particular phase of a cardiac cycle can, in principle, have a higher success rate for treating a cardiac rhythm disturbance than a stimulation which is delivered at a different point in time of the heart rhythm.

In one variant, the measurement variable is a hemodynamic measurement variable of the patient, an amplitude of an intracardiac electrogram, an amplitude of a far field signal, an amplitude of an electrocardiogram signal, an amplitude of an atrial signal, a systemic blood pressure, an arterial blood pressure, a venous blood pressure, a blood pressure in one of the ventricles, a pulmonary arterial pressure (PAP), another blood pressure, a change in one of the aforementioned blood pressures, a change in a morphology of a detected signal, an impedance change of a detected signal, a measurement value allowing a conclusion of a regularity or irregularity of the heart rhythm of the patient, a body position of the patient, a contractility of the heart muscle, or the change in the contractility of the heart muscle. As an alternative or in addition, the measurement variable can also be a variable that indicates or reflects one of the aforementioned variables.

A body position of the patient can, for example, be an upright position, a sitting position or a recumbent position (in particular a horizontal position). By selecting one or more of the aforementioned measurement variables, it is possible to take the current condition of the patient or the state of health of the patient into consideration in the selection of a suitable stimulation strategy. For example, if an increased blood pressure of the patient is detected, a stimulation strategy is selected which does not result in an increase in the blood pressure, so as not to further increase the already elevated blood pressure of the patient. Similarly, other physiological measurement variables of the patient may be used to select the stimulation strategy in such a way that a deviation of the respective measurement variable from a standard value or a standard range, a predefined value and/or an individual measurement value for the patient (for example a mean value, a median and the like) is not further amplified by the selected stimulation strategy.

In particular when the measurement variable is a hemodynamic measurement variable of the patient, it is provided in one variant that the measurement variable can be ascertained by the implantable system itself by way of the first detection unit or by way of a further detection unit. It is not necessary then to provide an additional sensor unit for detecting the measurement variable.

In another variant, however, such an additional sensor unit is provided, which is designed independently of the implantable system for stimulating the human heart or animal heart. Such an additional sensor unit makes it possible to determine not only hemodynamic parameters, but also other physiological parameters of the patient particularly easily, so that the possible physiological, pathophysiological or non-physiological measurement variables available for selecting the measurement variable can be expanded.

In one variant, the efficiency of the stimulation is a physiological efficiency. In particular the duration that is required to successfully treat an identified cardiac rhythm disturbance by way of the selected stimulation strategy is a measure suitable for determining the physiological efficiency. As an alternative or in addition, the efficiency can be a non-physiological efficiency, namely an efficiency for the energy required for the stimulation. Each implantable system for stimulating the human heart or animal heart comprises a power source, which contains a finite amount of energy. The service life of such systems decisively depends on the use of energy. If it is possible to lower the energy consumption, while keeping the success of the conducted stimulations at least the same, the service life of the stimulation system is increased. This is associated with considerable comfort for the patient since a surgical procedure for replacing the stimulation system or the power source of the stimulation system is not necessary until at a later time.

In one variant, stimulation strategies that in the past have proven to be particularly promising or efficient for a particular type of cardiac rhythm disturbance are given a higher priority than other stimulation strategies. When a renewed stimulation is carried out, these higher-priority stimulation strategies are then preferably selected for carrying out the stimulation. In this way, stimulation strategies that are expected to be successful can be predominantly applied. This typically increases the success or enhances the efficiency of the conducted stimulation. So as to carry out this variant, the program prompts the processor to store the selection criterion, the applied stimulation strategy and the success achieved thereby and/or the efficiency achieved thereby in the memory unit. Thereafter, the stored stimulation strategy is prioritized as a function of the achieved success and/or the achieved efficiency. This storage can take place, for example, in the form of a ranking table, wherein stimulation strategies that are listed higher in the ranking table have a higher prioritization than stimulation strategies listed further down, and are given preference in a subsequent selection of a suitable stimulation strategy. Other types of prioritization or hierarchization of the different available stimulation strategies are likewise conceivable.

So as not to carry out a treatment of a patient that is likely not very promising or not very efficient to begin with, or so as to utilize the energy available for the stimulations as efficiently as possible, it is provided in one variant to entirely exclude a stimulation strategy having a low prioritization at least temporarily from the stimulation strategies available for selection. For example, it is possible not to offer such a low-priority stimulation strategy as a stimulation strategy to be carried out for a first duration. The first duration can be a few minutes, hours or 2 to 5 days, for example. So as to implement such a temporary or permanent exclusion of individual stimulation strategies, the program prompts the processor in this variant to exclude a low-priority stimulation strategy, for a first duration, from the stimulation strategies to be carried out for an impending stimulation.

In one variant, the stimulation unit is an atrial stimulation unit, that is, a stimulation unit that is provided and configured for stimulating one atrium or both atria. In this variant, it is provided, in particular, that the conductable stimulation strategies are strategies by way of which atrial antitachycardia pacing (atrial ATP) can be applied. In one variant, the stimulation strategy to be carried out is cardioversion, in particular by an atrial treatment.

In one variant, the system for stimulating the heart is designed to take the ventricular activity of the heart into consideration in the selection of the atrial therapy. The reason behind this is that fundamental risks can exist for carrying out a stimulation therapy in the atria with the presence of ventricular tachycardia (VT). Specifically, so-called retrograde conduction can occur in the case of VT, that is, the VT is conducted back into the atrium via the cardiac stimulus conduction system and causes excitation of the atrium. The atrial excitation caused by VT cannot be terminated by an antitachycardia pacing therapy in the atrium. The pacemaker implant should therefore not interpret such an excitation as AT/AFib that can be terminated by atrial pacing. For this purpose, the ventricular activity has to be measured, and also has to be taken into consideration in the decision as to the use, type and timing of the atrial pacing therapy. For this purpose, it can be measured, for example, whether a high ventricular heart rate (that is, VT) is present. Known methods for identification by way of an ECG (intracardiac or surface ECG) can be employed for identifying retrograde conduction. For example, 2:1 retrograde conduction can be identified in a surface ECG in that P waves are visible after every other R wave. As a result, one embodiment of the present system for stimulating the heart is designed to determine the risk of retrograde conduction of ventricular tachycardia for the atria, and to adapt the stimulation to be delivered such that this risk is minimized to the extent possible. For this purpose, the program prompts the processor to initially determine a ventricular cardiac rhythm (that is, a ventricular activity) when the detected cardiac rhythm disturbance is atrial tachycardia. The risk of retrograde conduction of ventricular tachycardia in at least one atrium is then assessed based on the determined ventricular heart rhythm. A stimulation intended to treat the atrial tachycardia is then adapted as needed, in terms of time and/or location, taking the risk of retrograde conduction of ventricular tachycardia into consideration. Taking the ventricular activity into consideration in such a way can prevent atrial pacing from being delivered when the atrial excitation is caused by VT, and thus cannot be terminated by atrial pacing. When such a condition is identified, the system for stimulation according to the invention may, for example, not carry out or delay the atrial antitachycardia pacing therapy to be applied.

Within the scope of the assessment of the ventricular heart rhythm with respect to the risk of retrograde conduction, discrimination features, such as the ratio of atrial to ventricular rhythm or the ventricular signal morphology, are preferably derived and used to adapt the location and/or time for applying the atrial antitachycardia pacing therapy. It is possible to entirely suppress a planned atrial antitachycardia pacing therapy when the risk of retrograde conduction of ventricular tachycardia was assessed as being too high.

In one variant, the stimulation unit is provided and configured to carry out the stimulation in the form of electrical stimulation or in the form of optical stimulation. As a result, the stimulation unit offers different options for treating the previously detected cardiac rhythm disturbance. The decision as to which physical principle is selected for the corresponding treatment can be made, for example, by taking the severity of the detected cardiac rhythm disturbance into consideration.

One aspect of the present invention relates to a method for controlling the operation of an implantable system for stimulating a human heart or an animal heart. In particular, it is intended that the operation of an implantable system is controlled according to the above descriptions. This control method comprises the steps described hereafter.

First, it is checked by way of a first detection unit whether a cardiac rhythm disturbance is present in a cardiac region of a heart of a human patient or an animal patient.

Thereafter, a suitable stimulation strategy is selected. For this purpose, a selection criterion that includes a measurement variable or a variable calculated from a measurement variable is used. The measurement variable is a physiological measurement variable of the patient, a pathophysiological measurement variable of the patient and/or a non-physiological measurement variable indicating a state of the patient. A combination of different measurement variables is conceivable. Moreover, the different measurement variables can be arithmetically related to one another and, if needed, can also be given different weightings.

When a suitable stimulation strategy was selected, at least one impulse is generated in a stimulation unit for stimulating the cardiac region in which the cardiac rhythm disturbance was detected. The type, form and duration of the at least one impulse are decided based on the selected stimulation strategy. This strategy thus defines the pulse to be generated, and further designs the same.

Thereafter, data regarding a success and/or an efficiency of a conducted stimulation is collected and provided for further processing. This data is then compared to a predefinable success and/or efficiency criterion within the scope of the control method. If the predefinable success and/or efficiency criterion was achieved, no further method step is required. If, in contrast, the predefinable success and/or efficiency criterion was not achieved, the stimulation strategy is optimized. This optimization is used to achieve better success and/or greater efficiency during a subsequent stimulation using an optimized stimulation strategy. The optimization includes a change in the stimulation strategy with respect to at least one parameter. These parameters can be, for example, a form of the treatment, a number of the treatments, a combination of different treatments, a frequency of the treatments, and/or a point in time of the treatment. The aforementioned parameters can be used individually or in any arbitrary combinations with one another.

One aspect of the present invention relates to a computer program product including computer-readable code, which prompts a processor to carry out the steps described hereafter when the code is being executed on the processor.

First, it is detected by way of a first detection unit whether a cardiac rhythm disturbance is present in a cardiac region of a heart of a human patient or an animal patient.

Thereafter, a suitable stimulation strategy is selected based on a selection criterion. The selection criterion includes a measurement variable or a variable calculated from a measurement variable. The measurement variable can be a physiological measurement variable of the patient, a pathophysiological measurement variable of the patient and/or a non-physiological measurement variable indicating a state of the patient.

The program now prompts the processor to stimulate the cardiac region in which the cardiac rhythm disturbance was detected. This stimulation is carried out by way of a stimulation unit, wherein the manner of the stimulation is defined by the selected stimulation strategy.

Afterwards, a success and/or an efficiency of the conducted stimulation are detected.

This detected success and/or this detected efficiency are then compared to a predefinable success and/or efficiency criterion.

If the success and/or efficiency criterion—if necessary, within the scope of a likewise predefinable tolerance—was achieved, no further method step is required. If, in contrast, the predefinable success and/or efficiency criterion was not achieved, the stimulation strategy is optimized. This is used to achieve better success and/or greater efficiency during a subsequent stimulation using an optimized stimulation strategy. The optimization includes a change in the stimulation strategy with respect to at least one parameter. The parameter can be a form of the treatment, a number of the treatments, a combination of different treatments, a frequency of the treatments, and/or a point in time of the treatment. Arbitrary combinations and subsets of the aforementioned parameters can be taken into consideration.

One aspect of the present invention relates to a method for treating a human patient or an animal patient in need of such treatment. This method is carried out by way of an implantable system for stimulating the heart of the patient, wherein the system comprises a processor, a memory unit, a stimulation unit, and a first detection unit for detecting a cardiac rhythm disturbance in a cardiac region. The treatment method comprises the steps described hereafter.

First, it is detected by way of the first detection unit whether a cardiac rhythm disturbance is present in a cardiac region of a heart of a human patient or an animal patient.

When such a cardiac rhythm disturbance was detected, a suitable stimulation strategy is selected based on a selection criterion. The selection criterion includes a measurement variable or a variable calculated from the measurement variable. The measurement variable is a physiological measurement variable of the patient, a pathophysiological measurement variable of the patient and/or a non-physiological measurement variable indicating a state of the patient. It is possible to provide more than one measurement variable, wherein arbitrary combinations of the aforementioned measurement variables or of measurement variables from these measurement variable groups can be used.

Afterwards, the cardiac region in which the cardiac rhythm disturbance was detected is stimulated by way of the stimulation unit using the selected stimulation strategy.

Thereafter, a success and/or an efficiency of the conducted stimulation are detected. This can take place by way of the first detection unit or a further detection unit of the implantable system.

The detected success and/or the detected efficiency are then compared to a predefinable success and/or efficiency criterion.

If the predefinable success and/or efficiency criterion was achieved, no further method step is required. If, in contrast, the predefinable success and/or efficiency criterion was not achieved, the stimulation strategy is optimized, so that better success and/or greater efficiency can be achieved during a subsequent stimulation using an optimized stimulation strategy. The optimization includes a change in the stimulation strategy with respect to at least one parameter. This parameter is selected from the group consisting of a form of the treatment, a number of the treatment, a combination of different treatments, a frequency of the treatments, and a point in time of the treatment. This group can, in particular, consist of the aforementioned parameters. Arbitrary combinations and subsets of the aforementioned parameters are likewise conceivable.

All variants and alternative embodiments described in connection with the various implantable systems can be arbitrarily combined with one another and applied to the respective other systems. Similarly, they can also be applied in arbitrary combination to the described methods and the described computer program products. The described variants of the methods can further be arbitrarily combined with one another and applied to the respective other methods and to the computer program products and the systems. Similarly, the described variants of the computer program products can be arbitrarily combined with one another and applied to the respective other computer program products and to the described methods and the described systems.

Other features which are considered as characteristic for the invention are set forth in the appended claims.

Although the invention is illustrated and described herein as embodied in an implantable system for the diagnostic and/or therapeutic treatment of a human patient or an animal patient, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
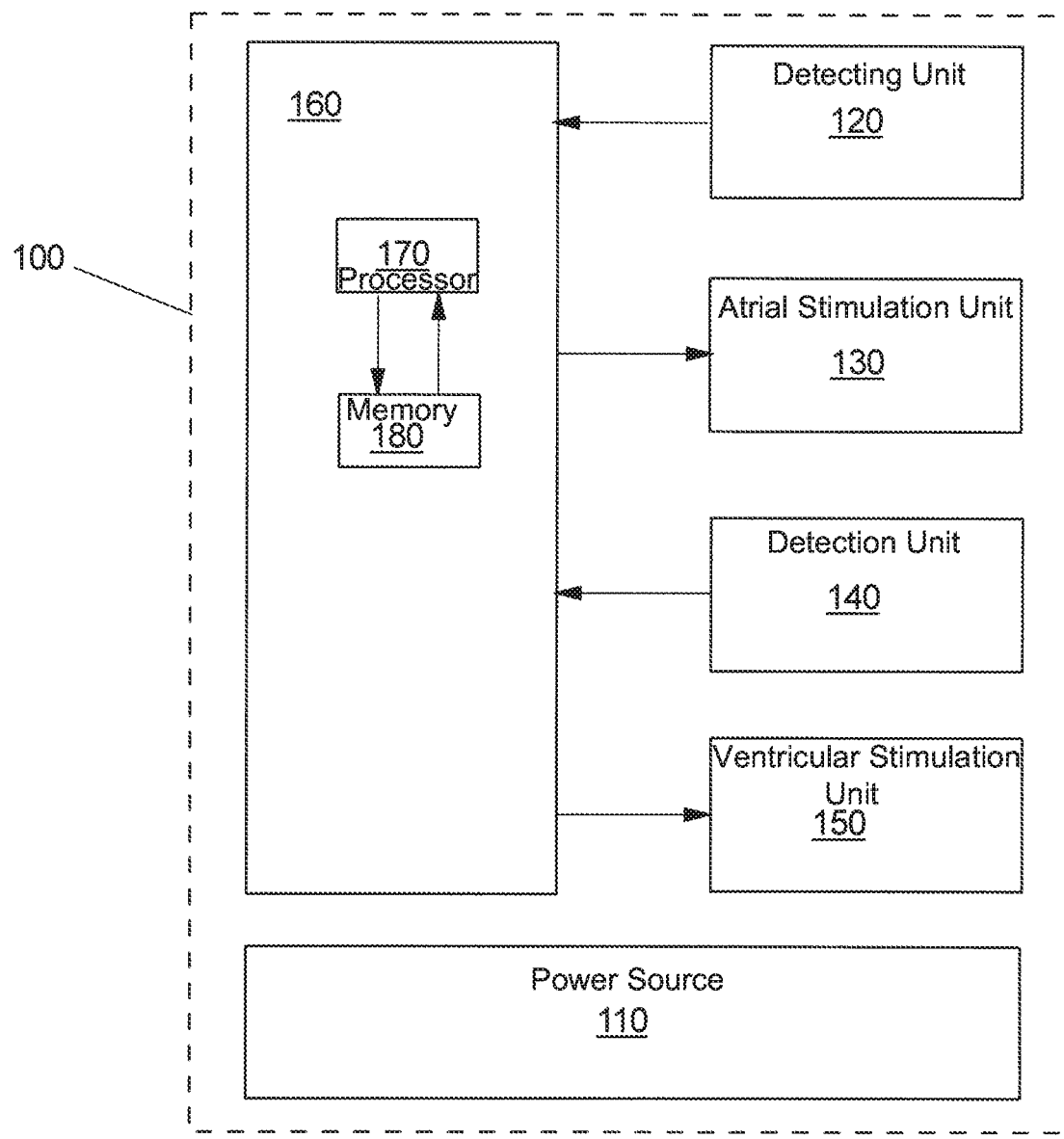
FIG. 1 is a block diagram of an exemplary embodiment of an implantable system for stimulating the human heart or animal heart.

Referring now to the figures of the drawings in detail and first, particularly to FIG. 1 thereof, there is shown a block diagram of an exemplary embodiment of a cardiac pacemaker 100, which is used as an implantable system for stimulating a human or animal heart. The cardiac pacemaker 100 comprises a power source 110, a first detection unit 120, an atrial stimulation unit 130, a second detection unit 140, and a ventricular stimulation unit 150. The first detection unit 120, the atrial stimulation unit 130, the second detection unit 140 and the ventricular stimulation unit 150 are operatively connected to a control unit 160. A processor 170 and a memory 180 are assigned to the control unit 160. The memory 180 includes program information prompting the processor 170 to carry out certain steps when the program is being executed on the processor 170.

These steps provide that it is detected by way of the first detection unit 120 whether atrial tachycardia to be treated is present in a human heart or an animal heart. When such atrial tachycardia requiring treatment is identified, the processor 170 prompts the ventricular stimulation unit 130 by way of the control unit 160 to carry out a ventricular conditioning stimulation of one ventricle or both ventricles. The effect of this ventricular conditioning stimulation is optionally detected by the second detection unit 140 and communicated to the processor 170 via the control unit 160. As the ventricular conditioning stimulation is being carried out by the ventricular stimulation unit 130 and/or thereafter, the processor 170, together with the control unit 160, ensures that the atrial stimulation unit 150 applies antitachycardia pacing to the (right) atrium of the heart to be treated.

The energy required for the operation of the individual components of the cardiac pacemaker 100 is provided by the power source 110.

Figure 2:
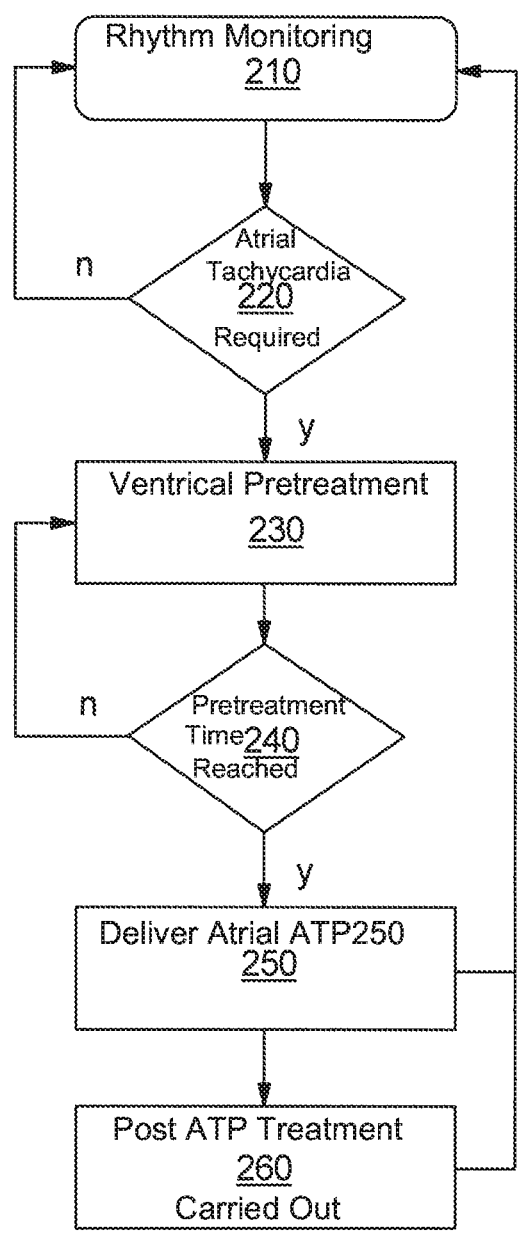
FIG. 2 is a schematic flow chart of an exemplary embodiment of an atrial antitachycardia therapy.

FIG. 2 shows the schematic flow chart of an exemplary embodiment of an atrial therapy, which can be carried out, for example, by way of the cardiac pacemaker 100 of FIG. 1.

In a first step, continuous rhythm monitoring 210 of the atrial rhythm of the patient wearing the cardiac pacemaker is carried out. If atrial tachycardia requiring treatment is established in a decision-making step 220 within the scope of this atrial rhythm monitoring 210, a ventricular pretreatment 230 is carried out. In FIG. 2 and in all figures that follow, the letter "n" denotes a negative decision or a negative result of a previously conducted check, whereas the letter "y" denotes a positive decision or a positive result of a previously conducted check.

The ventricular pretreatment 230 can be designed in the form of ventricular pacing, for example, which is triggered by every other atrial excitation and is delivered with a short AV delay of 10 ms, for example. A ventricular contraction is then already initiated in a phase where ventricular filling is still reduced. This ventricular contraction is thus carried out under reduced preload, so that a negative inotropic effect is achieved, briefly resulting in a reduced systemic blood pressure. The reduction in blood pressure thus generated increases the success of a concurrently or subsequently applied atrial ATP therapy.

The ventricular conditioning stimulation (ventricular pretreatment) is initially set until an established pretreatment time has been reached. It is thus checked in a checking step 240 whether the established pretreatment time has already been reached. If this is the case, atrial ATP 250 is subsequently delivered. After delivery of the atrial ATP 250, a post-ATP treatment 260 may optionally be carried out. As an alternative, the cardiac pacemaker can return or be reset to the continuous rhythm monitoring 210 again immediately after delivery of the atrial ATP 250.

Figure 3:
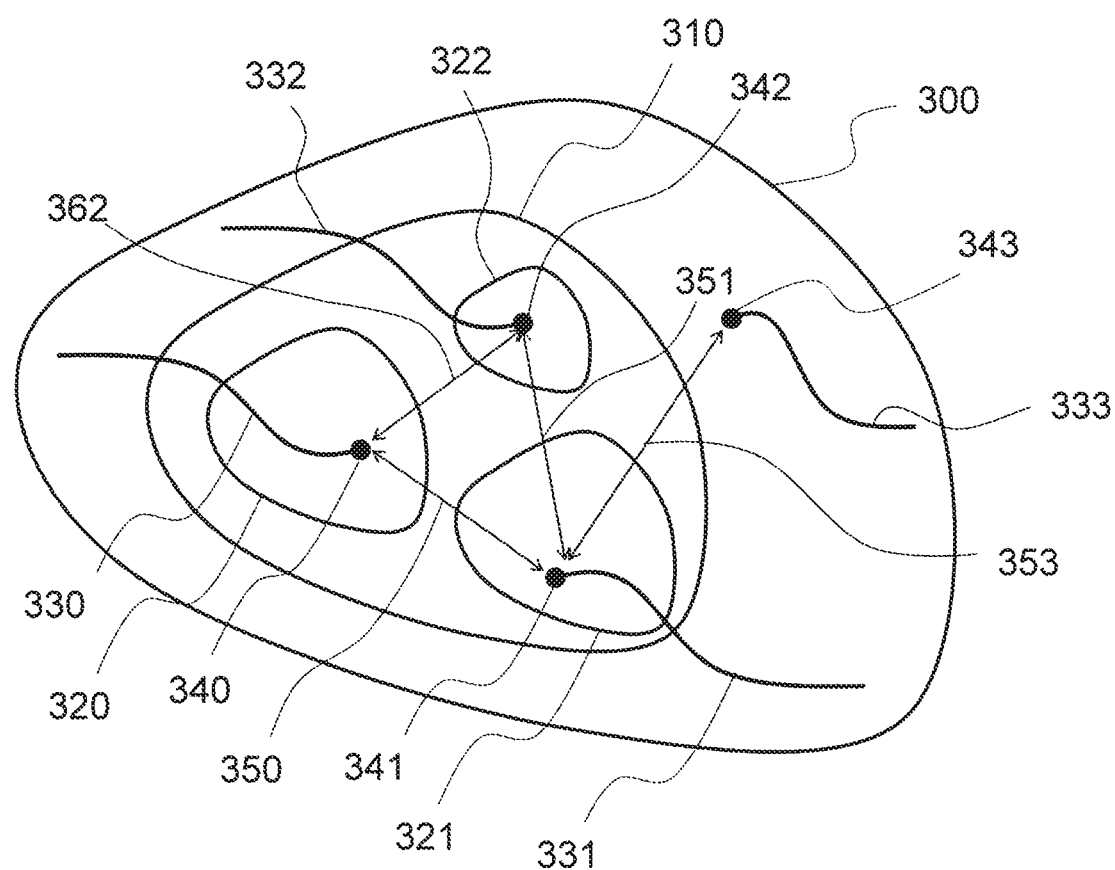
FIG. 3 is a schematic illustration of the arrangement of multiple electrodes in a human heart.

FIG. 3 shows a thorax 300 of a human patient, in whom a cardiac pacemaker was implanted as a system for treating the heart, to illustrate the functional principle of an electrode position determination. The heart 310 is schematically illustrated in a central region of the thorax 300. The heart 310 includes different cardiac regions 320, 321 and 322. This can be the left or right ventricle or an atrium of the heart 310, for example. A first electrode 330 is disposed in the first cardiac region 320. A second electrode 331 is disposed in the second cardiac region 321. Finally, a third electrode 332 disposed in the third cardiac region 322. The first electrode 330, the second electrode 331 and the third electrode 332 each include a conducting section 340, 341 and 342, which is disposed at the respective end and can also be referred to as an electrode pole.

Moreover, a fourth electrode 333, which likewise comprises a conducting section 343 at the end, is disposed outside the heart 310 in the region of the thorax 300.

A first distance 350 between the first electrode pole 340 of the first electrode 330 and the second electrode pole 341 of the second electrode 331 can now be determined. Similarly, a second distance 351 between the second electrode pole 341 of the second electrode 331 and the third electrode pole 342 of the third electrode 332 can be determined. Moreover, a third distance 352 between the first electrode pole 340 of the first electrode 330 and the third electrode pole 342 of the third electrode 332 can be determined. Likewise, it is possible to determine a distance between each of the electrode poles 340, 341, 342 and the reference electrode pole 343 of the reference electrode 342. Such a fourth distance 353 is only shown by way of example in FIG. 3 for the distance between the second electrode pole 341 of the second electrode 331 and the reference electrode pole 343 of the reference electrode 333.

The first electrode 330, the second electrode 331 and/or the third electrode 332 are only used for a cardiac treatment when the distances 350, 351, 352 and/or 353 are within predefinable ranges. If, in contrast, one of the ascertained distances 350, 351, 352 and/or 353 is too small or too large, a cardiac treatment is initially not carried out since the position of at least one electrode is inadequate.

Figure 4:
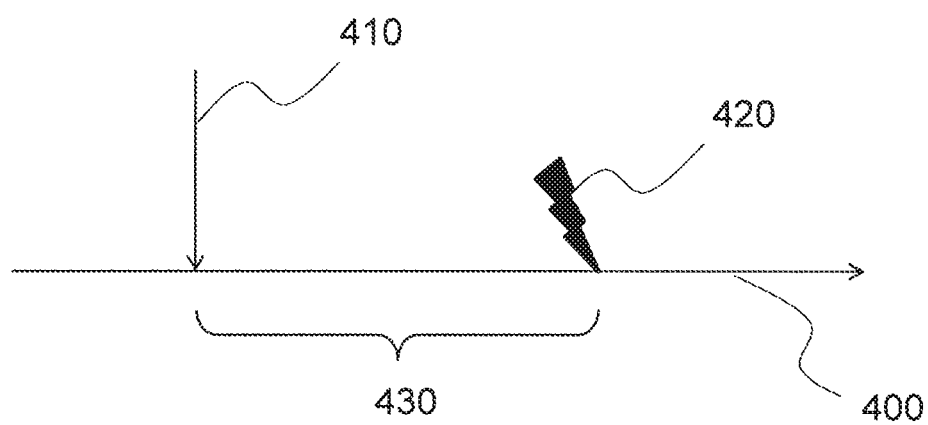
FIG. 4 is a schematic illustration of the chronological progression of an exemplary embodiment of a cardiac treatment.

FIG. 4 schematically shows the chronological progression of a cardiac treatment, in which first the position of a treatment electrode is checked. The events taking place are shown on a time axis 400. A therapy trigger 410 plans a specific cardiac therapy 420, which can also be referred to as cardiac treatment. This cardiac therapy 420 is planned by the therapy trigger 410 because previously a cardiac event which was classified as requiring treatment was established by way of a detection unit. Prior to the delivery of the cardiac therapy 420, however, it is checked during a time period 430 whether the positions of the electrodes required for the cardiac therapy 420 (see FIG. 3 in this regard) are adequate for the cardiac therapy 420. Only if this is the case is the cardiac therapy 420 actually carried out. Otherwise, the cardiac therapy 420 is at least initially suppressed from being conducted.

Figure 5:
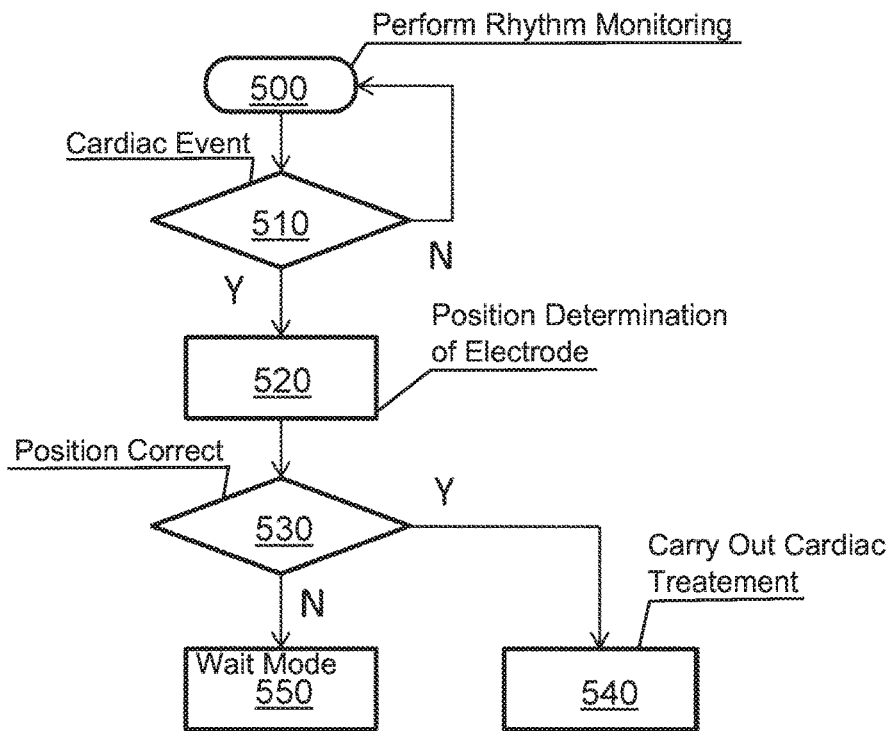
FIG. 5 is a flow diagram of an exemplary embodiment of a cardiac treatment.

FIG. 5 shows a flow diagram of a schematic flow of a method for treating a human heart or an animal heart, in which correct electrode positioning is checked before a cardiac therapy is carried out. In a first step, continuous rhythm monitoring 500 of the heart rhythm of the patient is carried out. If a cardiac event requiring treatment is established in the process, a position determination 520 of at least one treatment electrode of a cardiac pacemaker is initiated after a first decision-making step 510. Within the scope of this position determination 520, it is ascertained whether the position of the treatment electrode agrees with a predefinable reference position.

If it is established in a second decision-making step 530 that the position agrees with the reference position, a cardiac treatment 540 can be carried out, using the treatment electrode. If, in contrast, it is ascertained in the second decision-making step 530 that the established position of the treatment electrode does not agree with the expected position, the cardiac pacemaker is transferred into a wait mode 550. The cardiac pacemaker can be transferred from this wait mode 550 back into continuous rhythm monitoring 500. As an alternative, it is also possible to trigger a cardiac treatment manually, for example.

Figure 6:
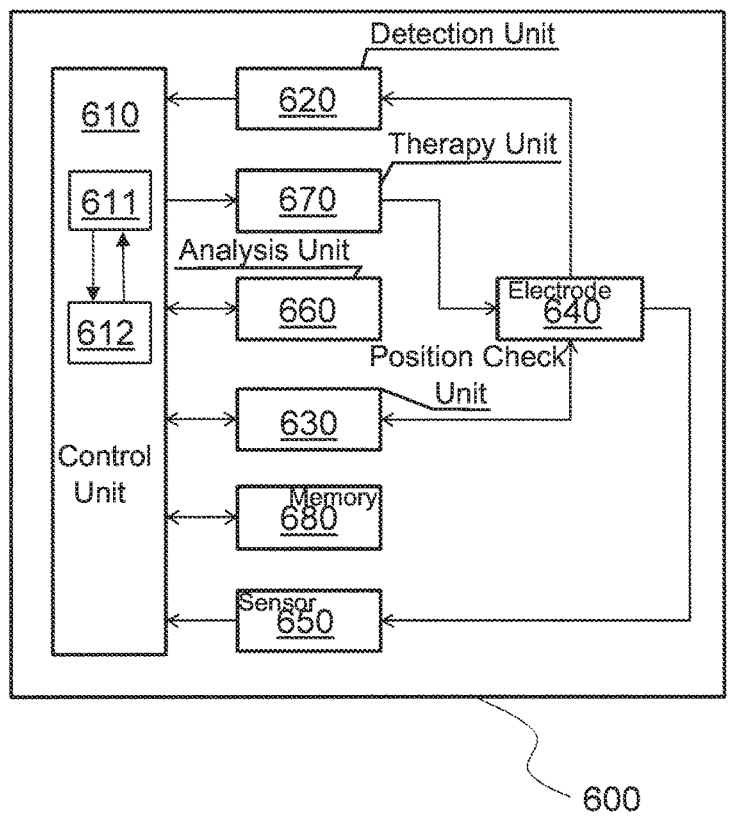
FIG. 6 is a simplified block diagram of an exemplary embodiment of a system for treating the human or animal heart.

FIG. 6 shows a simplified block diagram of an implantable cardiac pacemaker 600, which carries out a position determination of at least one treatment electrode. The cardiac pacemaker 600 serves as an implantable system for treating a human heart or an animal heart. It comprises a control unit 610, which is equipped with a processor 611 and a memory unit 612. A detection unit 620 checks whether a cardiac event to be treated has occurred in the human or animal heart of the patient in whom the cardiac pacemaker 600 was implanted. The detection unit 620 transmits the result of this check to the control unit 610.

When a cardiac event to be treated has occurred, the processor 611 prompts a position check unit 630, by way of the control unit 610, to check the position of a treatment electrode 640. For this purpose, the position check unit 630 compares the established position of the electrode 640 to a reference position. Additional data, which provides insights into the position of the treatment electrode 640, using an additional position sensor or acceleration sensor 650 can be used in the process.

The data provided by the position determination unit 630, and optionally by the additional sensors 650, is evaluated in an analysis unit 660. If it is found in the process that the position of the treatment electrode 640 corresponds to a position adequate for the impending cardiac therapy, the processor 611, by way of the control unit 610, activates a therapy unit 670, which delivers a therapy adequate for treating the cardiac event to the corresponding cardiac region by way of the treatment electrode 640.

The data regarding the position of the treatment electrode 640 collected by the position determination unit 630 can be stored, together with a piece of time information, in a trend memory 680 so as to be able to evaluate or identify a trend of the change in position of the treatment electrode 640.

When the analysis unit 660 establishes an inadequate position of the treatment electrode 640, the therapy unit 670 is not activated for the delivery of a cardiac treatment. Rather, initially no cardiac treatment is carried out.

The treatment electrode 640 can moreover simultaneously act as a detection electrode and thus already be used together with the detection unit 620 in the detection of a cardiac event to be treated.

Not all units shown in the block diagram of FIG. 6 necessarily have to form separate units within the cardiac pacemaker 600. Rather, the processor 611 can assume numerous tasks if it receives appropriate program information from the memory 612.

Figure 7:
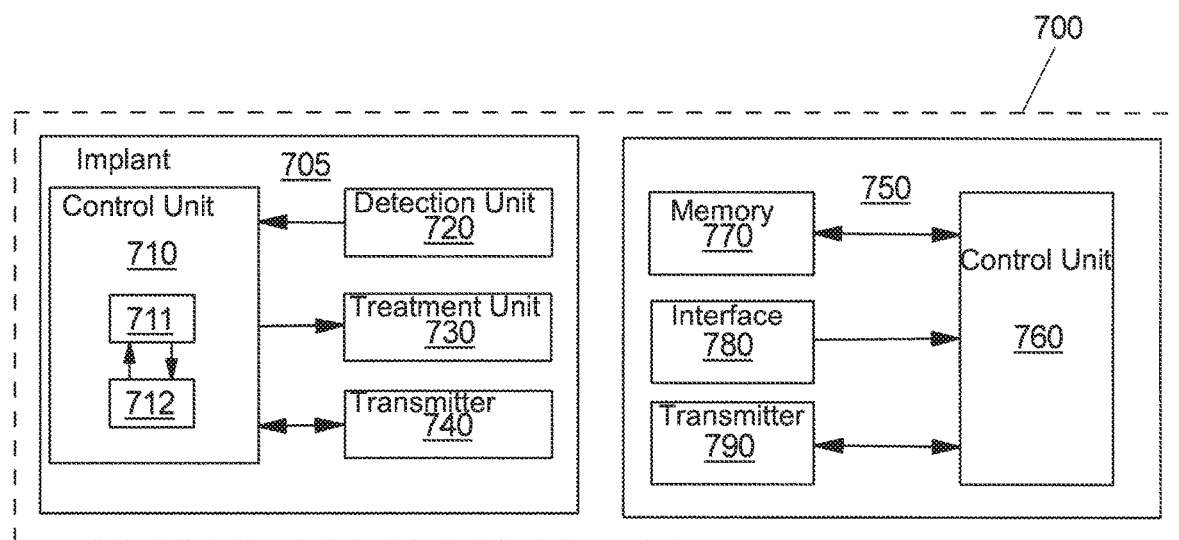
FIG. 7 is a block diagram of an exemplary embodiment of a treatment system for the diagnostic and/or therapeutic treatment of a patient.

FIG. 7 shows an exemplary embodiment of a treatment system 700 comprising an implant 705, which serves as an implantable system for the diagnostic and/or therapeutic treatment of a human patient or an animal patient. The implant 705 comprises a first control unit 710 including a first processor 711 and a first memory unit 712. Furthermore, a detection unit 720 is provided, which checks a particular physiological parameter of a patient in whom the implant 705 is implanted. For example, a heart rhythm of the patient can be monitored by the detection unit 720. In addition, the implant 705 comprises a treatment unit 730, which can be used to carry out a diagnostic and/or therapeutic treatment of the patient. This treatment unit 730 includes a plurality of different treatment functionalities, which each define a particular treatment. A treatment functionality may also specify a sequence of certain diagnostic and/or therapeutic treatments.

The implant 705 furthermore comprises a first remote data transmission unit 740 by way of which data can be transmitted and/or received by the control unit 710 or the processor 711. The remote data transmission unit 740 preferably operates wirelessly.

In addition, the treatment system 700 comprises a remote access unit 750, which is disposed remotely from the implant 705. The remote access unit 750 can be set up in a hospital or a doctor's office, for example. By way of the remote access unit 750, it is possible to establish communications contact with the implant 705. For this purpose, the remote access unit 750 comprises a second processor 760, a second memory unit 770, a user interface 780 and a second remote data transmission unit 790.

The second processor 760 is able to retrieve program information from the second memory unit 770 so as to subsequently carry out a corresponding program. By way of the user interface 780, it is possible to carry out inputs for the further processing of data by the second processor 760. For example, a physician can manually prompt a reactivation of a previously deactivated treatment functionality by way of the user interface 780. The second processor 760 can then transmit reactivation data to the first data transmission unit 740 of the implant 705 via the second remote data transmission unit 790. When the first processor 711 of the implant 705 receives such reactivation data, it can forward this data to the treatment unit 730 and reactivate a previously deactivated treatment functionality of the treatment unit 730.

The implant 705 and the remote access unit 750 can be disposed several meters, several kilometers, but also hundreds or thousands of kilometers apart from one another. By selecting appropriate data transmission protocols, reliable communication between the first data transmission unit 740 disposed in the implant 705 and the second remote data transmission unit 790 disposed in the remote access unit 750 can nonetheless be ensured.

Figure 8:
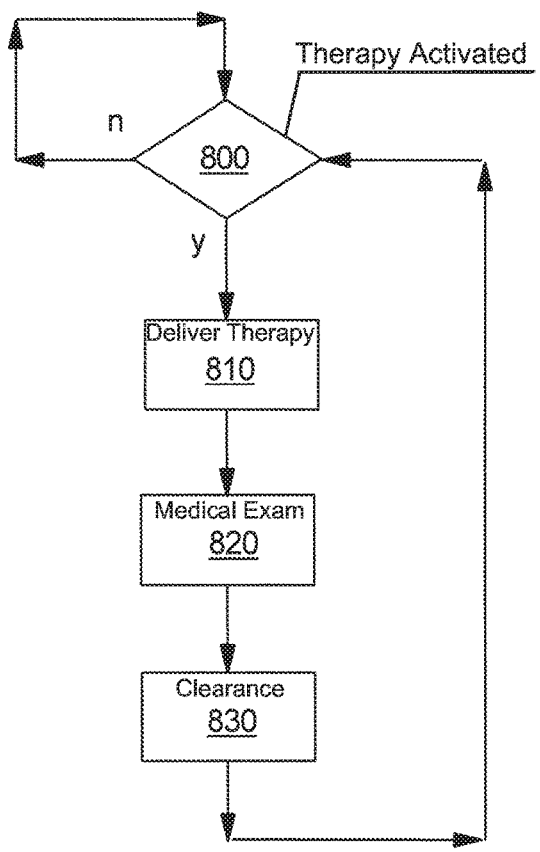
FIG. 8 is a flow diagram of a schematic flow of an exemplary method carried out by an exemplary embodiment of an implantable system for the diagnostic and/or therapeutic treatment of a patient.

FIG. 8 shows a flow chart to schematically illustrate an exemplary flow of a method that can be carried out by an exemplary embodiment of an implantable system for the diagnostic and/or therapeutic treatment of a human patient or an animal patient, such as by the implant 705 of FIG. 7.

This flow chart refers to the specific application in the field of atrial antitachycardia pacing. This means that it is assumed, within the scope of the exemplary embodiment illustrated in FIG. 8, that the implant is a cardiac pacemaker, that is, a system for stimulating the human heart or animal heart.

In a first step 800, it is checked whether the delivery of an atrial antitachycardia therapy is activated. Such a delivery of an atrial antitachycardia therapy represents a treatment functionality that the treatment or stimulation unit of the corresponding implant can carry out. If it is established during this check that the delivery of an atrial antitachycardia therapy is cleared, such an atrial antitachycardia therapy 810 can be delivered.

After expiration of a presettable time, which is 48 hours in the exemplary embodiment described here, the further delivery of atrial antitachycardia pacing is suppressed. The reason is that, if atrial antitachycardia pacing is required over such an extended time period, the patient's risk of thrombosis increases as a result of the atrial tachycardia still not being successfully treated. The patient now has to visit his or her primary care physician for a medical examination 820. The patient receives an anticoagulation drug therapy within the scope of this examination. The administration of anticoagulation pharmaceuticals lowers the patient's risk of thrombosis again. This information that the patient received such an anticoagulation therapy is forwarded to an implantation physician, that is, a physician specialized in implants, such as cardiac pacemakers. This implantation physician can then reactivate the option of delivering of an atrial antitachycardia pacing therapy within the scope of a clearance 830 by way of remote access. For this purpose, the physician transmits clearance data to the cardiac pacemaker of the patient, which results in a reactivation of the deactivated treatment functionality.

It is then possible to deliver atrial antitachycardia pacing therapies again, should this still be necessary based on the state of the patient's heart. In the event that the atrial heart rhythm of the patient has since normalized again, the option of delivering atrial antitachycardia pacing therapies nonetheless remains activated. If atrial tachycardia reoccurs, a corresponding atrial antitachycardia treatment can then be carried out.

Figure 9:
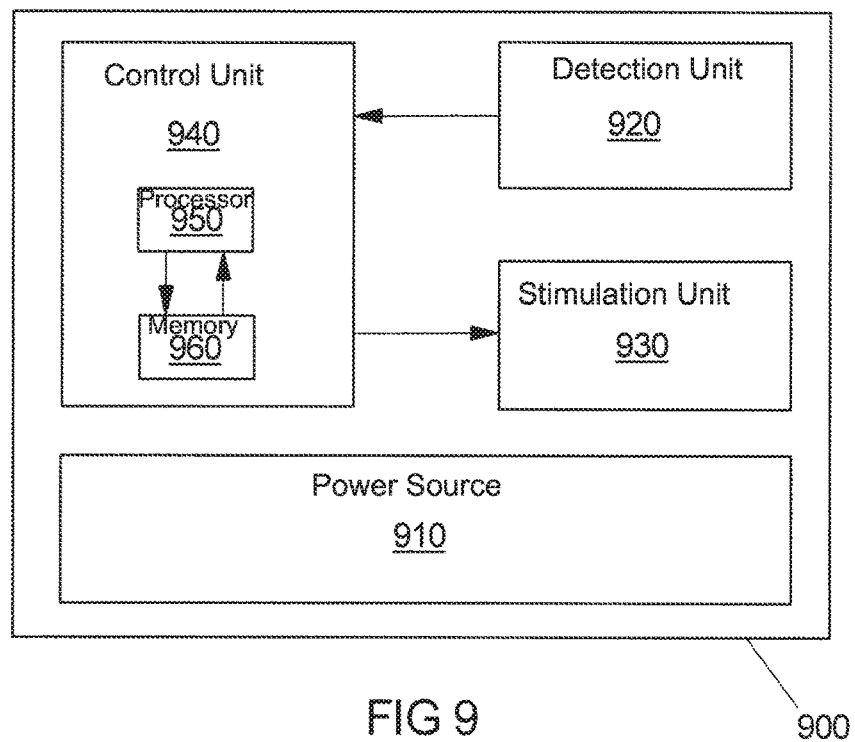
FIG. 9 is a block diagram of an exemplary embodiment of an implantable system for stimulating the human heart or animal heart.

FIG. 9 shows a block diagram of an exemplary embodiment of a cardiac pacemaker 900, which is used as an implantable system for stimulating the human or animal heart. The cardiac pacemaker 900 comprises a power source 910 which supplies the individual components of the cardiac pacemaker 900 with electric energy. Moreover, the cardiac pacemaker 900 comprises a detection unit 920, an atrial stimulation unit 930 and a control unit 940, which is operatively connected to both the detection unit 920 and the atrial stimulation unit 930. A processor 950 and a memory unit 960, which are operatively connected to one another, are assigned to the control unit 940. The memory unit 960 includes program information prompting the processor 950 to carry out certain steps when the program is being executed on the processor 950.

In the specific case of the exemplary embodiment of FIG. 9, the processor 950 retrieves program information from the memory unit 960, which prompts the processor first to query information from the detection unit 920 as to whether atrial tachycardia was detected in a human heart or an animal heart. When this is the case, the processor prompts the atrial stimulation unit 930 to apply atrial antitachycardia pacing to the affected atrium. Thereafter, the processor 950 prompts the atrial stimulation unit 930 to carry out an atrial post-treatment stimulation so as to increase the effect of the applied atrial antitachycardia pacing therapy. For this purpose, the processor 950 can initially retrieve additional information from the detection unit 920 as to whether the previously detected atrial tachycardia was terminated by the atrial antitachycardia pacing that was already applied. The processor can suspend the atrial post-treatment stimulation from being carried out by way of the atrial stimulation unit 930 until positive information was ascertained on the part of the detection device 920 with respect to a termination of the previously detected atrial tachycardia.

Figure 10:
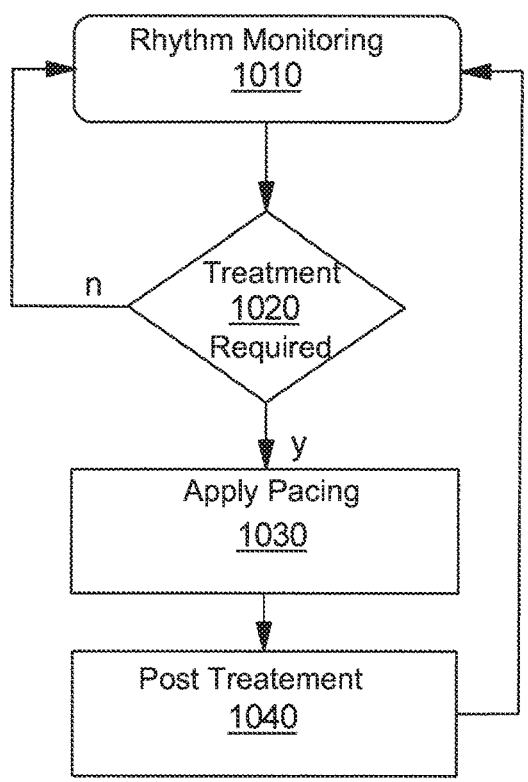
FIG. 10 is a schematic flow chart of an exemplary embodiment of an atrial antitachycardia therapy.

FIG. 10 shows a schematic flow chart of an exemplary embodiment of an atrial therapy, which can be carried out, for example, by way of the cardiac pacemaker 900 of FIG. 9.

In a first step, continuous rhythm monitoring 1010 of the atrial rhythm of a patient wearing the cardiac pacemaker is carried out. If it is established in a decision-making step 1020, within the scope of this atrial rhythm monitoring 1010, that atrial tachycardia requiring treatment is present, atrial antitachycardia pacing 1030 is subsequently applied or delivered, which can also be referred to as atrial ATP. Afterwards, an atrial post-treatment 1040 is carried out, which can also be referred to as ATP post-treatment. This post-treatment is carried out using a lower stimulation rate than for the atrial antitachycardia pacing 1030, but the rate is still greater than the normal (intrinsic) atrial heart rate.

After completion of the atrial post-treatment stimulation 1040, the cardiac pacemaker is returned into a mode of continuous rhythm monitoring 1010. The decision as to when the atrial post-treatment stimulation 1040 is ended can be made, for example, as a function of an elapsed time or as a function of a certain number of cardiac cycles of the patient.

Figure 11:
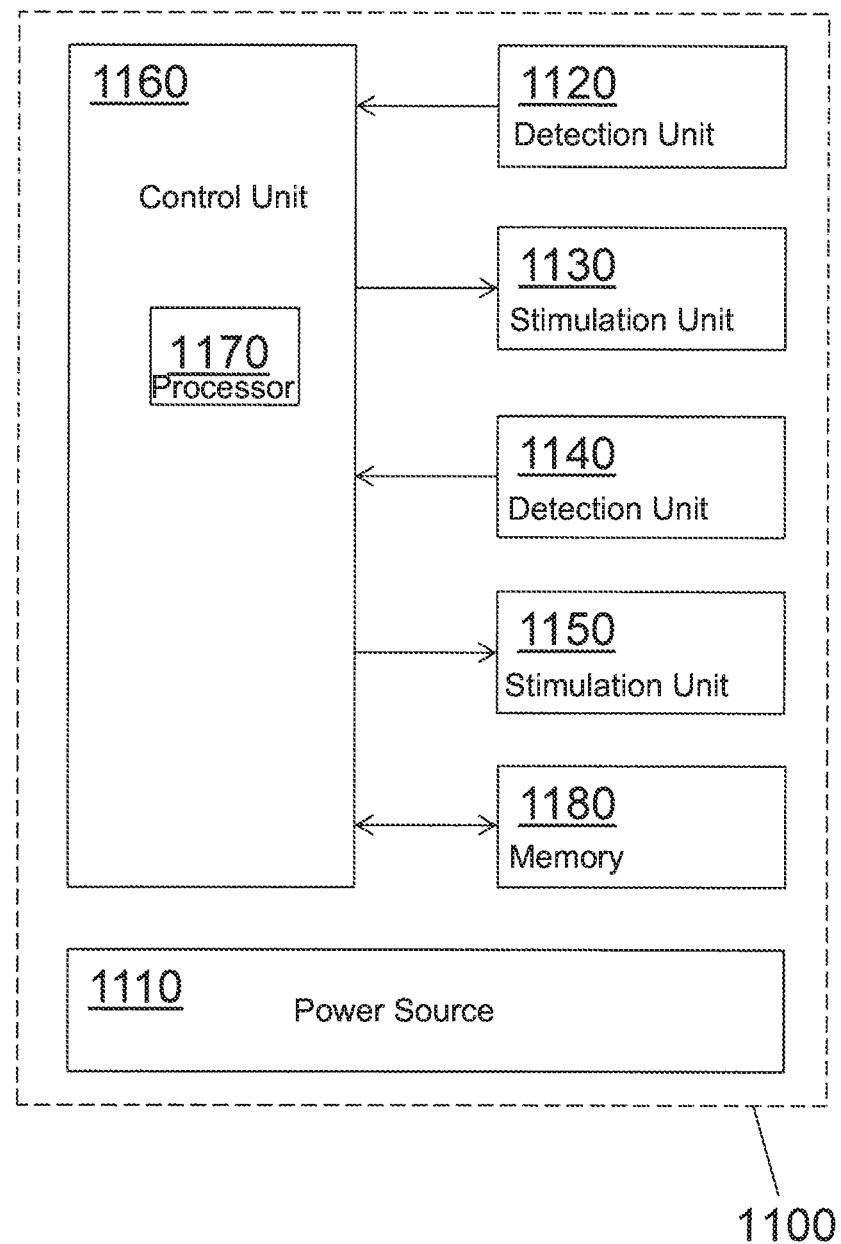
FIG. 11 is a block diagram of an exemplary embodiment of an implantable system for stimulating the human heart or animal heart.

FIG. 11 shows a block diagram of a cardiac pacemaker 1100, which serves as an implantable system for stimulating the human or animal heart. The cardiac pacemaker 1100 comprises a power source 1110, an atrial detection unit 1120, an atrial stimulation unit 1130, a ventricular detection unit 1140, a ventricular stimulation unit 1150 and a control unit 1160. A processor 1170 and a data memory 1180 are assigned to the control unit 1160. The processor 1170 is able to retrieve data from the data memory 1180, for example so that a program can be executed on the processor 1170. The atrial detection unit 1120, the atrial stimulation unit 1130, the ventricular detection unit 1140 and the ventricular stimulation unit 1150 are operatively connected to the control unit 1160, so that the processor is able to receive signals from the individual units or send signals to the individual units.

A success or an efficiency of a stimulation previously carried out by way of the atrial stimulation unit 1130 or the ventricular stimulation unit 1150 can be stored in the data memory 1180. Typically, the stimulation strategy underlying the corresponding stimulation and the cardiac rhythm disturbance previously detected by the atrial detection unit 1120 and/or the ventricular detection unit 1140 are also stored. In addition, it is possible to assign a priority criterion to the individual data sets comprising the detected cardiac rhythm disturbance, the applied stimulation strategy and the achieved success or achieved efficiency, and to store this together with the data sets. In this way, it is possible to assign a higher priority to data sets that relate to a particularly successful or particularly efficient stimulation.

Figure 12:
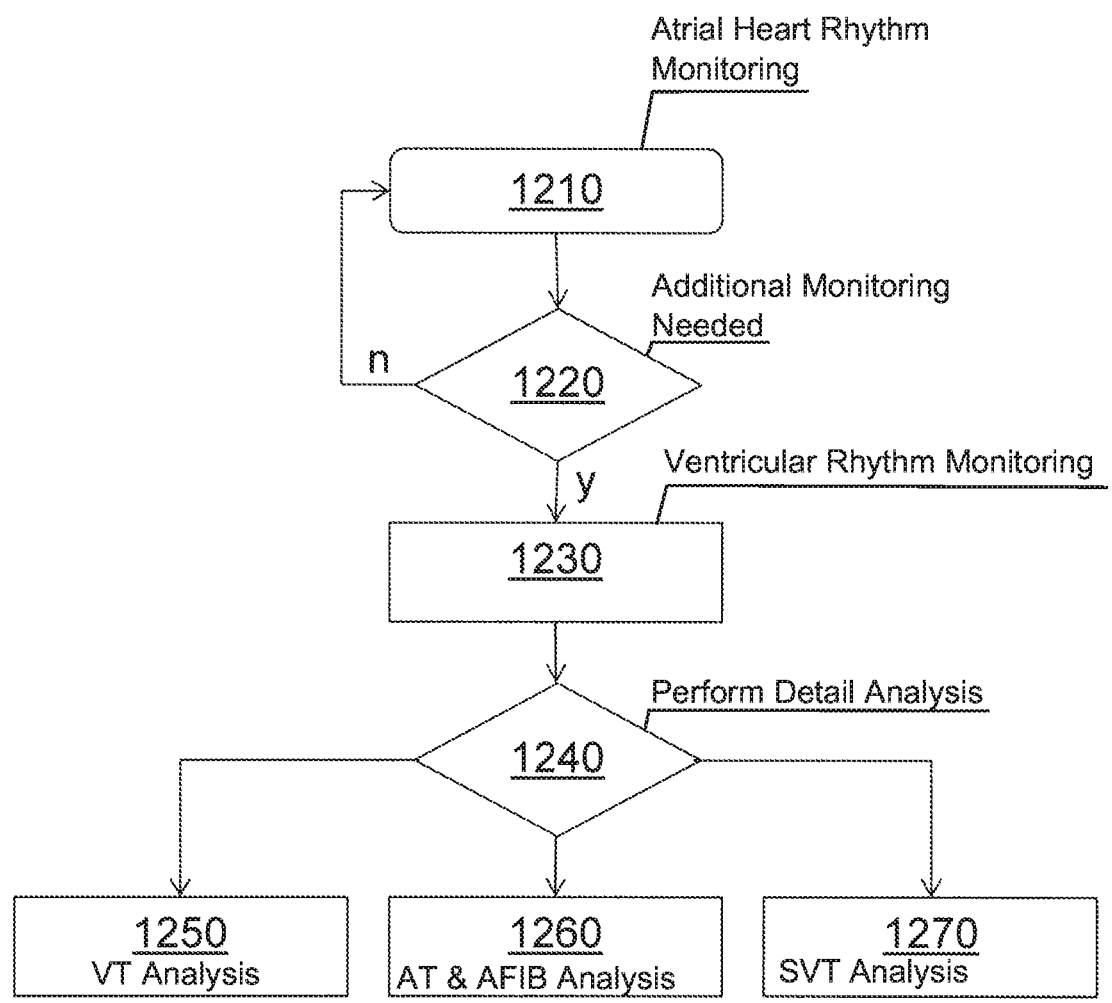
FIG. 12 is a schematic flow chart of an exemplary embodiment of the detection of a cardiac rhythm disturbance.

FIG. 12 shows a schematic flow chart for a method which can be used to distinguish different cardiac rhythm disturbances from one another. This method can be carried out by a cardiac pacemaker, such as the cardiac pacemaker 1100 of FIG. 11.

In a first step 1210, continuous rhythm monitoring of the atrial heart rhythm of the patient in whom the corresponding cardiac pacemaker was implanted is carried out. When atrial tachyarrhythmia or atrial tachycardia is established within the scope of this continuous rhythm monitoring 1210 in a decision-making step 1220, additionally monitoring 1230 of the ventricular rhythm of the patient is carried out.

In a subsequent decision-making step 1240, a more detailed analysis of the detected atrial rhythm and of the detected ventricular rhythm with respect to the resulting heart rhythm and the atrioventricular conduction (AV conduction) takes place. The resulting heart rhythm is divided into three rhythm categories 1250, 1260 and 1270. The first rhythm category 1250 encompasses a presence of VT or also of VT with retrograde conduction. The second rhythm category 1260 encompasses atrial tachycardia/tachyarrhythmia (AT) and atrial fibrillation (AFib). The third rhythm category 1270 encompasses anterograde conduction of atrial tachycardia/tachyarrhythmia and supraventricular tachycardia (SVT).

Only when a resulting heart rhythm of the second category 1260 was detected, that is, a heart rhythm that encompasses atrial tachycardia/tachyarrhythmia or atrial fibrillation, is a stimulation strategy subsequently selected which includes atrial antitachycardia pacing. The details of the delivery of this atrial antitachycardia pacing therapy are shown in greater detail in FIG. 13.

Figure 13:
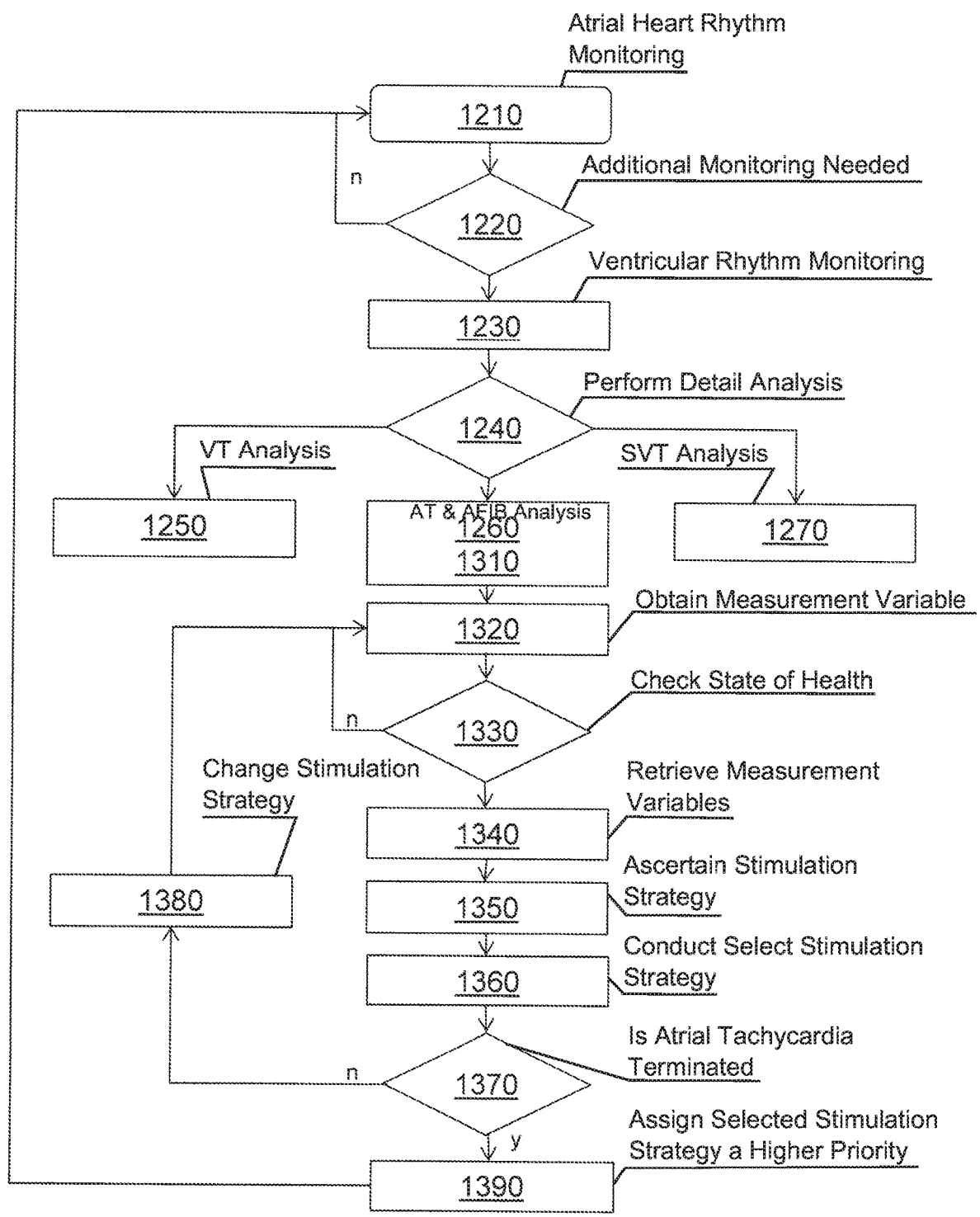
FIG. 13 is a schematic flow chart of an exemplary embodiment of a treatment of a cardiac rhythm disturbance by way of stimulation, including upstream detection of the cardiac rhythm disturbance.

The upper portion of FIG. 13 initially shows the method steps which are already known from FIG. 12. The reference numerals used already in FIG. 12 were used again in the process. Reference is made to the above description of FIG. 12 with respect to a more detailed description.

When a heart rhythm of the second category 1260 is identified in the categorization of the resulting heart rhythm, that is, a heart rhythm that encompasses atrial tachycardia or atrial fibrillation, a workflow for atrial antitachycardia pacing is activated 1310.

Initially, at least one measurement variable, namely a physiological measurement variable of the patient and/or a pathophysiological measurement variable of the patient, and/or a non-physiological measurement variable indicating a condition of the patient, is ascertained 1320. This may be a measurement variable that specifies the body position of the patient, for example. This measurement variable or a variable calculated from this measurement variable would then be used to form a selection criterion. This selection criterion, in the broadest sense, takes the state of health of the patient into consideration.

Thereafter, it is checked in a checking step 1330 whether the condition or the state of health of the patient meets the fundamental requirements for a stimulation. It is thus checked whether suitable stimulation strategies exist for the formed selection criterion. If this is not the case, (initially) no pacing is applied. Additional measurement variables can then be detected so as to characterize the condition of the patient in even more detail and form a new selection criterion.

When the measurement variable or the measurement variables that were used for the selection criterion show that the patient meets the necessary requirements for the impending atrial antitachycardia pacing therapy, the overstimulation therapies available in the internal data memory of the cardiac pacemaker are retrieved in a subsequent selection step 1340. In a further selection step 1350, the stimulation strategies that best meet the conditions or measurement variables of the patient ascertained in the ascertainment step 1320 are then selected from the available overstimulation therapies or stimulation strategies. So as to ascertain which stimulation strategies best correspond to the previously ascertained measurement variable, in particular the form, the design and the composition of the available stimulation strategies are taken into consideration. Moreover, the success rate during prior applications of the stimulation strategies can be taken into consideration. The selected stimulation strategy or strategies is or are then delivered to the patient in a stimulation delivery step 1360, wherein the sequence of the delivered stimulations results from the prior prioritization thereof.

In a further checking step 1370, it is subsequently checked whether the conducted stimulation(s) has/have resulted in a termination of the atrial tachycardia. If this is not the case, a change is made in an optimization step 1380 to the previously conducted stimulation strategy or to the selected stimulation strategies still to be conducted. This adaptation is made based on a parameter, such as the treatment form, the treatment number, the combination of different treatments, the treatment frequency and the treatment point in time. It is also noted in the internal data memory of the cardiac pacemaker that the non-adapted stimulation strategy was not successful. The priority value thereof is lowered in this connection. This means that the priority of this stimulation strategy is decreased. In contrast, the priority value of the adapted (that is, optimized) stimulation strategy can initially remain unchanged. When it was ascertained that a successful termination of the previously detected atrial tachycardia is possible by the optimized stimulation strategy, the priority criterion of the corresponding stimulation strategy can be increased. This stimulation strategy is then preferably applied during a later treatment.

Finally, when it was established in the decision-making step 1370 that a termination of the atrial tachycardia has taken place, this success is stored, together with the details of the applied stimulation strategy (in particular the stimulation form, stimulation design and stimulation composition) and the underlying selection criterion or the measurement variables defining the selection criterion, in the internal data memory of the cardiac pacemaker. In addition, the information that this stimulation strategy was successful is stored there. Moreover, this stimulation strategy is assigned a higher priority value. This takes place in the memory step 1390. Thereafter, the cardiac pacemaker is returned into a mode of continuous rhythm monitoring 1210.

As a result of a suitable categorization of a detected cardiac rhythm disturbance, a selection of suitable stimulation strategies based on measurement variables related to the condition of the patient, and a prioritization and an optimization of the different stimulation strategies, ultimately an extremely efficient treatment of cardiac rhythm disturbances can be carried out. This treatment has a considerably lower energy requirement than the treatments known from the prior art. The reason is that stimulation strategies that are not very promising for the respective detected cardiac rhythm disturbance are not applied to begin with, as a result of an optimization and prioritization of different stimulation strategies. This reduces the energy expenditure of the corresponding cardiac pacemaker and thereby extends the service life thereof.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. An implantable system for a diagnostic and/or therapeutic treatment of a heart of a patient including a human patient or an animal patient, the implantable system comprising:
   a processor;
   a treatment unit;
   a remote data transmitter;
   a memory storing a computer-readable program, which prompts said processor to carry out the following steps when the computer-readable program is being executed on said processor:
       delivering, by said treatment unit, atrial antitachycardia stimulation to the heart of the patient and then reducing a risk of thrombosis by deactivating an ability of said treatment unit to deliver further atrial antitachycardia stimulation after an expiration of a presettable time, the presettable time being a time period of about 48 hours and after which an unsuccessful treatment of atrial tachycardia increases the patient's risk of thrombosis;

receiving reactivation data by way of said remote data transmitter; and reactivating the ability of said treatment unit to subsequently deliver the further atrial antitachycardia stimulation based on the reactivation data that was received.

2. The implantable system according to claim 1, wherein the computer-readable program prompts said processor to transmit status data by way of said remote data transmitter which indicates whether a particular treatment functionality of said treatment unit is activated or deactivated.

3. The implantable system according to claim 1, wherein the computer-readable program prompts said processor to permit a reactivation of treatment functionalities assigned to a first group, based on received reactivation data, and/or to disallow a reactivation of treatment functionalities assigned to a second group, based on the received reactivation data.

4. The implantable system according to claim 3, wherein said memory stores assignment data for assigning the treatment functionalities to the first group or to the second group, and wherein the computer-readable program prompts said processor to assign the treatment functionalities to the first group or to the second group based on the assignment data.

5. The implantable system according to claim 4, further comprising a near field telemetry unit, and the computer-readable program prompts said processor to receive the assignment data by way of said near field telemetry unit.

6. The implantable system according to claim 1, wherein the implantable system is configured for treating a human heart or an animal heart.

7. A treatment system, comprising:
an implantable system for a diagnostic and/or therapeutic treatment of a heart of a patient including a human patient or an animal patient, said implantable system containing a first processor, a first memory, a treatment unit and a first remote data transmitter;
a remote access unit disposed remotely from said implantable system, said remote access unit containing a second processor, a second memory and a second remote data transmitter;
said first memory storing a first computer-readable program, which prompts said first processor to carry out the following steps when the first computer-readable program is being executed on said first processor:
delivering, by said treatment unit, atrial antitachycardia stimulation to the heart of the patient and then reducing a risk of thrombosis by deactivating an ability of said treatment unit to deliver further atrial antitachycardia stimulation after an expiration of a presettable time, the presettable time being a time period of about 48 hours and after which an unsuccessful treatment of atrial tachycardia increases the patient's risk of thrombosis;
receiving reactivation data by way of the first remote data transmitter; and
reactivating the ability of said treatment unit to subsequently deliver the further atrial antitachycardia stimulation based on the reactivation data that was received; and
said second memory unit storing a second computer-readable program, which prompts said second processor to carry out the following steps when the second computer-readable program is being executed on said second processor:
generating the reactivation data in response to an input or a program request; and
transmitting the reactivation data by way of the second remote data transmitter.

8. The treatment system according to claim 7, wherein the second computer-readable program prompts said second processor to receive status data of said implantable system prior to a generation of the reactivation data by way of the second remote data transmitter, which indicates whether a particular treatment functionality of said treatment unit is activated or deactivated.

9. A method for controlling an operation of an implantable system for a diagnostic and/or therapeutic treatment of a heart of a patient including a human patient or an animal patient, which comprises the following steps of:
delivering, by a treatment unit of the implantable system, atrial antitachycardia stimulation to the heart of the patient and then reducing a risk of thrombosis by deactivating an ability of the treatment unit to deliver further atrial antitachycardia stimulation after an expiration of a presettable time, the presettable time being a time period of about 48 hours and after which an unsuccessful treatment of atrial tachycardia increases the patient's risk of thrombosis;
receiving reactivation data by way of a remote data transmission unit; and
reactivating the ability of the treatment unit to subsequently deliver the further atrial antitachycardia stimulation based on the reactivation data that was received.

10. A non-transitory computer medium storing a computer program product having computer-readable code, which prompts a processor to carry out the following steps when the computer-readable code is being executed on the processor:
delivering, by a treatment unit of an implanted system, atrial antitachycardia stimulation to a heart of a patient and then reducing a risk of thrombosis by deactivating an ability of the treatment unit to deliver further atrial antitachycardia stimulation after an expiration of a presettable time, wherein the implanted system is configured at least for a therapeutic treatment of a heart of a patient, including a human patient or an animal patient, the presettable time being a time period of about 48 hours and after which an unsuccessful treatment of atrial tachycardia increases the patient's risk of thrombosis;
receiving reactivation data by way of a remote data transmission unit; and
reactivating the ability of the treatment unit to subsequently deliver the further atrial antitachycardia stimulation based on the reactivation data that was received.

11. A method for treating a patient including a human patient or an animal patient requiring treatment, by way of an implantable system which performs a diagnostic and/or therapeutic treatment of the human patient or the animal patient, the implantable system containing a processor, a memory, a treatment unit and a remote data transmitter, the method comprises the following steps of:
delivering, by the treatment unit of the implantable system, atrial antitachycardia stimulation to the heart of the patient and then reducing a risk of thrombosis by deactivating an ability of the treatment unit to deliver further atrial antitachycardia stimulation after an expiration of a presettable time, the presettable time being a time period of about 48 hours and after which an unsuccessful treatment of atrial tachycardia increases the patient's risk of thrombosis;
receiving reactivation data by way of the remote data transmitter;

reactivating the ability of the treatment unit to subsequently deliver the further atrial antitachycardia stimulation based on the reactivation data that was received; and delivering, by the treatment unit, the further atrial antitachycardia stimulation to the patient.

\* \* \* \* \*